(12) United States Patent
Yoshitomo et al.

(10) Patent No.: US 7,858,819 B2
(45) Date of Patent: Dec. 28, 2010

(54) TRIS(FORMYLPHENYL) AND NOVEL POLYNUCLEAR PHENOL DERIVED THEREFROM

(75) Inventors: Akira Yoshitomo, Wakayama (JP); Tatsuya Iwai, Wakayama (JP)

(73) Assignee: Honshu Chemical Industry Co., Ltd., Tokyo (JP)

(*) Notice: Subject to any disclaimer, the term of this patent is extended or adjusted under 35 U.S.C. 154(b) by 0 days.

(21) Appl. No.: 12/304,085

(22) PCT Filed: Jun. 11, 2007

(86) PCT No.: PCT/JP2007/061733

§ 371 (c)(1),
(2), (4) Date: Aug. 19, 2009

(87) PCT Pub. No.: WO2007/142353

PCT Pub. Date: Dec. 13, 2007

(65) Prior Publication Data

US 2010/0099908 A1    Apr. 22, 2010

(30) Foreign Application Priority Data

Jun. 9, 2006 (JP) .............................. 2006-161693
Jun. 20, 2006 (JP) .............................. 2006-170574

(51) Int. Cl.
C07C 47/57 (2006.01)
C07C 59/74 (2006.01)
C07C 69/66 (2006.01)
C07C 69/76 (2006.01)

(52) U.S. Cl. .................... 560/53; 562/463; 568/442; 568/720

(58) Field of Classification Search ............... 560/53; 562/463; 568/442, 720
See application file for complete search history.

(56) References Cited

FOREIGN PATENT DOCUMENTS

| JP | 62-84035 | 4/1987 |
| JP | 03-048249 | 3/1991 |
| JP | 06-312947 | 11/1994 |
| JP | 07-268049 | 10/1995 |
| JP | 11-199533 | 7/1999 |
| JP | 2000-212130 | 8/2000 |
| JP | 2000-309561 | 11/2000 |
| JP | 2001-312055 | 11/2001 |
| JP | 2006-078640 | 3/2006 |
| WO | WO 2004/050231 A2 | 6/2004 |

*Primary Examiner*—Sikarl A Witherspoon
(74) *Attorney, Agent, or Firm*—Knobbe Martens Olson & Bear LLP

(57) ABSTRACT

A new tris(formylphenyl) of the following general formula and polynuclear phenol derived therefrom:

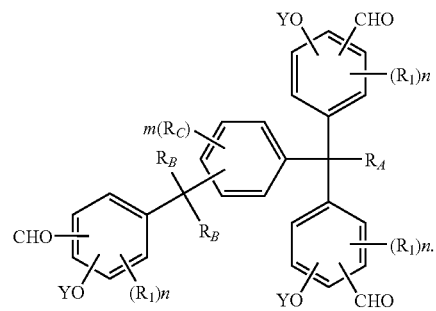

13 Claims, No Drawings

TRIS(FORMYLPHENYL) AND NOVEL POLYNUCLEAR PHENOL DERIVED THEREFROM

This application is the U.S. National Phase under 35 U.S.C. §371 of International Application PCT/JP2007/061733, filed Jun. 11, 2007, which claims priority to Japanese Patent Application No. 2006-161693, filed Jun. 9, 2006, and No. 2006-170574, filed Jun. 20, 2006. The International Application was published under PCT Article 21(2) in a language other than English.

TECHNICAL FIELD

The present invention relates to a novel tris(formylphenyl) and novel polynuclear phenol derived therefrom. To be specific, it relates to a novel tris(formylphenol) having one formyl group and one hydroxy group as nuclear substitution groups at each terminal phenyl nucleus of the molecule; a novel tris(ether-formylphenyl) having one formyl group and one ether group as nuclear substitution groups at each terminal phenyl nucleus of the molecule; and a polynuclear phenol compound constituted by either of the aforementioned tris(formylphenyl) where each formyl group is substituted by two phenol groups.

PRIOR ART

Among trihydroxyphenyl compounds having a substitution group or groups, Japanese Patent Laid-open No. Sho 62-84035 describes a compound constituted by 1-[α-methyl-α-(4'-hydroxyphenyl)ethyl]-4-[α',α'-bis(4''-hydroxyphenyl)ethyl]benzene where three hydroxyphenyl nuclei in the molecule are each substituted by one or two methyl groups or chlorine atoms.

Japanese Patent Laid-open No. Hei 3-48249 describes a compound constituted by 1-[α-methyl-α-(4'-hydroxyphenyl)ethyl]-4-[α',α'-bis(4''-hydroxyphenyl)ethyl]benzene where three hydroxyphenyl nuclei in the molecule are each substituted by a methyl group, aryl group, hydroxyl group or chlorine atom.

Also, Japanese Patent Laid-open No. Hei 6-312947 describes an adduct mixture constituted by 1,1,1-tris(4-hydroxyphenyl)methane having three to six hydroxybenzyl groups per molecule. In addition, Patent Laid-open No. WO 2004/050231 A2 describes a polynuclear formylphenol constituted by 1,3,5-tris[(5-tert-butyl-3-formyl-4-hydroxyphenyl)ethynyl]benzene and a method for production thereof.

Furthermore, compounds constituted by a polynuclear polyphenol compound with its hydroxyl group etherified by various compounds, being produced by alkoxy-carbonyl-methyl-etherifying the hydroxyl group of triphenol methane, are described in Japanese Patent Laid-open Nos. 2000-212130 and 2000-309561, while compounds constituted by a polynuclear polyphenol compound having two or more trihydroxyphenylmethane skeletons in the molecule, with its hydroxyl group etherified by various compounds, are described in Japanese Patent Laid-open Nos. 2001-312055 and 2006-78640.

However, trisformylphenyl compounds having an asymmetrical structure and not having any unsaturated bond other than aromatic rings have not been known. Also, because trisphenyl compounds, having such formyl group as a nuclear substitution group have excellent reactivity with an aromatic compound such as a phenol, they are useful as a material for phenol resins and other modifiers and photoresists, intermediate material for various polynuclear polyphenol compounds obtained by reaction with a phenol, or reactive intermediate material for polynuclear aromatic compounds offering excellent heat resistance, among others.

In addition, tris(ether-formylphenyl) compounds having an asymmetrical structure and also having ether and formyl groups as nuclear substitution groups at each phenyl nucleus have not been known. These trisphenyl compounds having ether and formyl groups as nuclear substitution groups where the hydrocarbon group bonded with the ether group is a carboxyhydrocarbon group or alkoxycarbonyl hydrocarbon group, provide excellent reactivity with phenols, etc., due to the formyl group or excellent reactivity due to the terminal ester group or carboxyl group, and are therefore useful as a material for phenol resins and other modifiers and photoresists, intermediate material for various polynuclear phenol compounds obtained by reaction with a phenol, or reactive intermediate material for polynuclear aromatic compounds offering excellent heat resistance, among others.

On the other hand, various polynuclear phenol compounds have been known, such as a compound having two tris(hydroxyphenyl)methane skeletons in the molecule as described in Japanese Patent Laid-open No. Hei 11-199533, and such polynuclear polyphenol compound, according to the inventors of the present invention, have been found to have a glass transition temperature near 140° C. However, polynuclear phenol compounds offering even higher glass transition temperatures and various performances are also required.

A polynuclear phenol obtained from a novel tris(formylphenyl) conforming to the present invention is expected to offer excellent heat resistance, but no such polynuclear phenol compound was heretofore known. Also, such polynuclear phenol compound is useful as a material for EUV and other photosensitive resist compositions, epoxy resin material or hardener, developer or anti-fade agent used in thermosensitive recording materials, or sterilizer, fungicide, antioxidant, etc.

Patent Literature 1: Japanese Patent Laid-open No. Sho 62-84035
Patent Literature 2: Japanese Patent Laid-open No. Hei 3-48249
Patent Literature 3: Japanese Patent Laid-open No. Hei 6-312947
Patent Literature 4: Japanese Patent Laid-open No. Hei 11-199533
Patent Literature 5: Patent Laid-open No. WO 2004/050231 A2
Patent Literature 6: Japanese Patent Laid-open No. 2000-212130
Patent Literature 7: Japanese Patent Laid-open No. 2000-309561
Patent Literature 8: Japanese Patent Laid-open No. 2001-312055
Patent Literature 9: Japanese Patent Laid-open No. 2006-78640

SUMMARY OF THE INVENTION

Problems to be Solved by the Invention

The present invention was made in light of the aforementioned conditions relating to conventional polynuclear polyphenol compounds, and is intended to provide a novel tris(formylphenyl) having one formyl group and one hydroxy group or ether group as nuclear substitution groups at each phenyl nucleus, or specifically a novel tris(ether-formylphenyl) having a formyl group as a nuclear substitution group at the phenyl nucleus, especially tris(4-ether-3-formylphenyl), as well as a polynuclear polyphenol where each formyl group of said tris(formylphenyl) is substituted by two phenol groups.

Means for Solving the Problems

A novel trisformylphenyl conforming to the present invention is expressed by General Formula (1) specified below.

[Chemical 1]

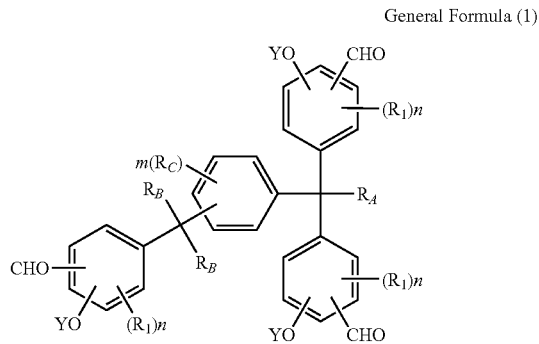

General Formula (1)

In the formula, Y represents a hydrogen atom or —$R_2COOR_3$ group, $R_2$ represents a monocyclic or condensed cyclic aromatic hydrocarbon group with a carbon atom number of 6 to 15 or an aliphatic hydrocarbon group with a carbon atom number of 1 to 8 that may have in its main chain a monocyclic or condensed cyclic aromatic hydrocarbon group with a carbon atom number of 6 to 15, and $R_3$ represents a hydrogen atom or alkyl group with a carbon atom number of 1 to 6. $R_1$ s may be the same or different and respectively represent a hydrogen atom, alkyl group with a carbon atom number of 1 to 8 or alkoxyl group with a carbon atom number of 1 to 8. $R_B$ and $R_C$ may be the same or different, where $R_A$, $R_B$ and $R_C$ respectively represent a hydrogen atom or alkyl group with a carbon atom number of 1 to 6 and n and m are respectively an integer of 0 or 1 to 3.

If Y in a trisformylphenyl expressed by the aforementioned General Formula (1) is a hydrogen atom, then the aforementioned General Formula (1) represents a trisformylphenol expressed by General Formula (2) specified below.

[Chemical 2]

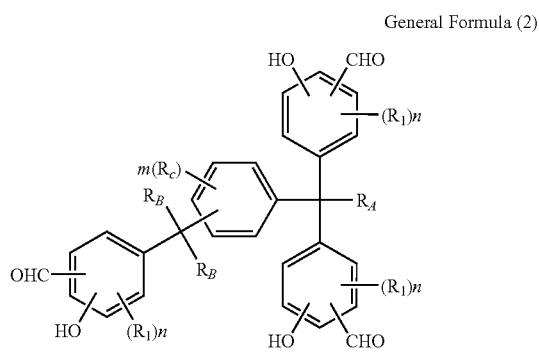

General Formula (2)

In the formula, $R_1$, $R_A$, $R_B$, $R_C$, n and m are the same as the items represented by the corresponding symbols in General Formula (1).

To be specific, $R_1$s in the formula may be the same or different and respectively represent a hydrogen atom, alkyl group with a carbon atom number of 1 to 8 or alkoxyl group with a carbon atom number of 1 to 8. Specific examples include, among others, straight- or branched-chain or cyclic alkyl groups such as methyl group, ethyl group, propyl group, butyl group, t-butyl group, pentyl group, 3-methylpentyl group, cyclopropyl group, cyclopentyl group, 3-methylcyclopentyl group, cyclohexyl group, 2,4-dimethylcyclohexyl group and cycloheptyl group. Examples of an alkoxyl group with a carbon atom number of 1 to 8 include, among others, straight- or branched-chain or cyclic alkoxyl groups such as methoxy group, ethoxy group, propoxy group, isopropoxy group, butoxy group, t-butoxy group, pentyloxy group, isopentyloxy group, cyclopropoxy group, cyclopentyloxy group, 3-methylcyclopentyloxy group, cyclohexyloxy group, 2,4-dimethylcyclohexyloxy group and cycloheptyloxy group. Among the above, straight- or branched-chain alkyl or alkoxyl groups with a carbon atom number of 1 to 4 or cyclic alkyl or cyclic alkoxyl groups with a carbon atom number of 5 to 7 are desirable, of which straight- or branched-chain alkyl groups with a carbon atom number of 1 to 4 are particularly desirable.

$R_B$ and $R_C$ may be the same or different, where $R_A$, $R_B$ and $R_C$ respectively represent a hydrogen atom or alkyl group with a carbon atom number of 1 to 6 and n and m are respectively an integer of 0 or 1 to 3. $R_A$, $R_B$ and $R_C$ are specifically a hydrogen atom, methyl group, ethyl group, isopropyl group, n-propyl group, n-butyl group, tert-butyl group or n-hexyl group. Desirable alkyl groups for $R_A$ and $R_B$ include, among others, primary or secondary alkyl groups, of which alkyl groups with a carbon atom number of 1 to 3 are more desirable. $R_C$ should desirably be a hydrogen atom or methyl group. n should desirably be 1 or 2 and m be 0 or 1.

The substitution position of the hydroxyl group should be the p- or o-position, or desirably p-position, relative to the position where the phenyl group bonds with the carbon atom bonding with $R_A$ or $R_B$, and the substitution position of the formyl group should be the o- or p-position, or desirably o-position, relative to the hydroxyl group. If $R_A$ is an alkyl group, the substitution position of the hydroxyl group of the phenyl group that bonds with the hydrocarbon atom bonding with $R_A$ should desirably be the p-position of that bonding position. Also when both $R_B$S are alkyl groups, the substitution position of the hydroxyl group of the phenyl group that bonds with the hydrocarbon atom bonding with $R_B$ should desirably be the p-position of that bonding position to facilitate synthesis. Accordingly, a desirable structure is expressed by General Formula (3) specified below.

[Chemical 3]

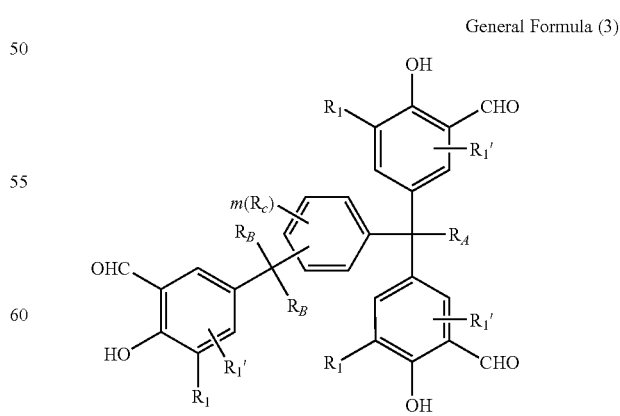

General Formula (3)

In the formula, $R_A$, $R_B$, $R_C$, $R_1$ and m are the same as the items represented by the corresponding symbols in General Formula (1). $R_1'$ is the same as $R_1$ in General Formula (1) and represents a hydrogen atom, alkyl group with a carbon atom number of 1 to 8 or alkoxyl group with a carbon atom number of 1 to 8.

In General Formula (3), $R_1'$ is specifically the same as $R_1$ in General Formula (2), where desirable alkyl groups include, among others, primary and secondary alkyl groups, of which straight- or branched-chain alkyl groups with a carbon atom number of 1 to 4 are more desirable, while desirable alkoxy groups include, among others, straight- or branched-chain alkoxy groups with a carbon atom number of 1 to 4. If $R_A$ is an alkyl group, $R_1'$ should desirably be a hydrogen atom for easy synthesis; m should desirably be 0 for cost effectiveness and easy availability, etc.; and methyl groups are particularly desirable for $R_A$ and $R_B$. Accordingly, a more desirable structure is expressed by General Formula (4) specified below, and yet a more desirable structure is expressed by General Formula (5) specified below.

[Chemical 4]

General Formula (4)

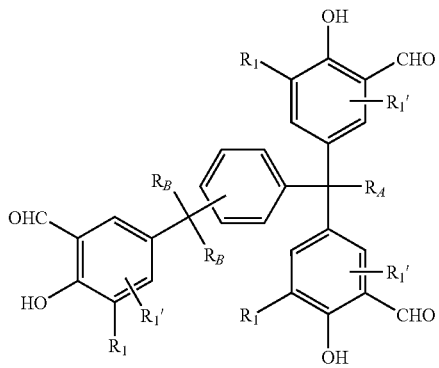

In the formula, $R_A$, $R_B$ and $R_1$ are the same as the items represented by the corresponding symbols in General Formula (1), and $R_1'$ is the same as $R_1$ in General Formula (1).

[Chemical 5]

General Formula (5)

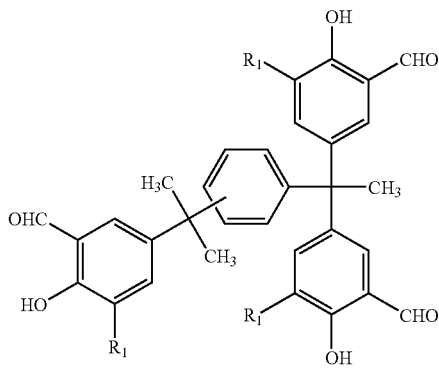

In the formula, $R_1$ is the same as the item represented by the corresponding symbol in General Formula (1).

Also in General Formula (5), the substitution position relative to the α,α-bis (3-formyl-4-hydroxyphenyl)ethyl group in the α-methyl-α-(3-formyl-4-hydroxyphenyl)ethyl group may be changed to the ortho, meta or para position, of which the para or meta position is desirable.

Accordingly, specific examples of a trisformylphenol group conforming to the present invention include the following, among others:

1-[α-methyl-α-(3-formyl-5-methyl-4-hydroxyphenyl) ethyl]-4-[α,α-bis(3-formyl-5-methyl-4-hydroxyphenyl) ethyl]benzene (Compound 1);

[Chemical 6]

(Chemical Formula 1)

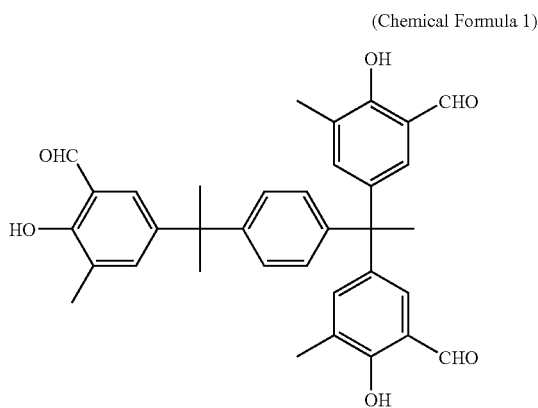

1-[α-methyl-α-(3-formyl-4-hydroxyphenyl)ethyl]-4-[α,α-bis(3-formyl-4-hydroxyphenyl)ethyl]benzene (Compound 2);

[Chemical 7]

(Chemical Formula 2)

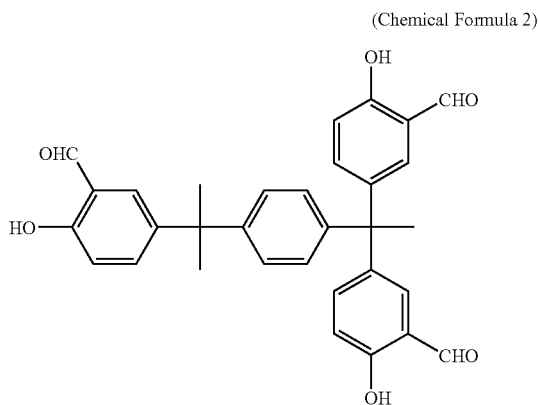

1-[α-methyl-α-(3-formyl-5-ethyl-4-hydroxyphenyl)ethyl]-4-[α,α-bis(3-formyl-5-ethyl-4-hydroxyphenyl)ethyl]benzene (Compound 3);

[Chemical 8]

(Chemical Formula 3)

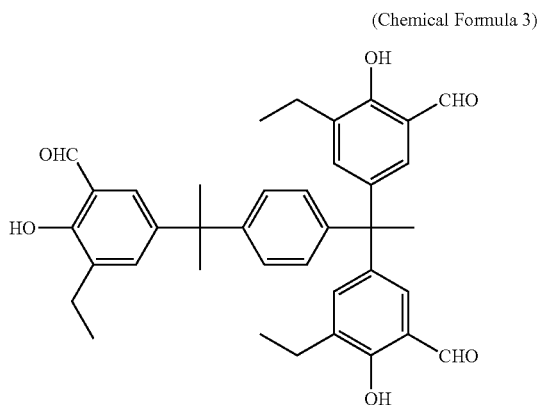

1-[α-methyl-α-(3-formyl-5-cyclohexyl-4-hydroxyphenyl)
ethyl]-4-[α,α-bis(3-formyl-5-cyclohexyl-4-hydroxyphenyl)ethyl]benzene (Compound 4);

[Chemical 9]

(Chemical Formula 4)

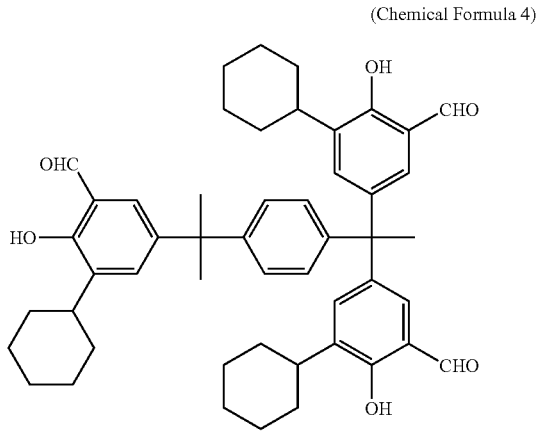

1-[α-methyl-α-(3-formyl-5-t-butyl-4-hydroxyphenyl)
ethyl]-4-[α,α-bis(3-formyl-5-t-butyl-4-hydroxyphenyl)ethyl]benzene (Compound 5);

[Chemical 10]

(Chemical Formula 5)

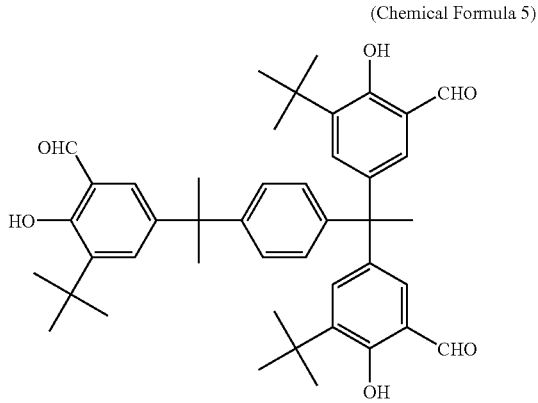

1-[α-methyl-α-(3-formyl-5-isopropyl-4-hydroxyphenyl)
ethyl]-4-[α,α-bis(3-formyl-5-isopropyl-4-hydroxyphenyl)ethyl]benzene (Compound 6); and

[Chemical 11]

(Chemical Formula 6)

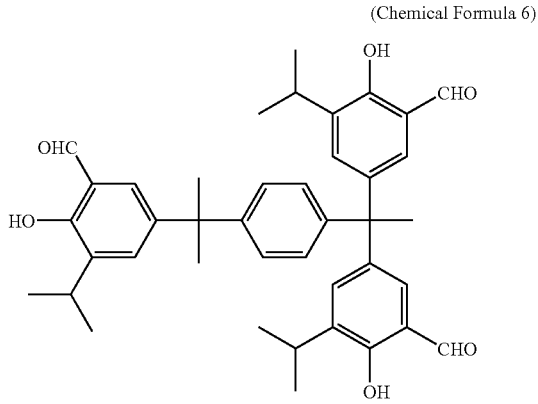

1-[α-methyl-α-(3-formyl-5-methyl-4-hydroxyphenyl)
ethyl]-3-[α,α-bis(3-formyl-5-methyl-4-hydroxyphenyl)ethyl]benzene (Compound 7).

[Chemical 12]

(Chemical Formula 7)

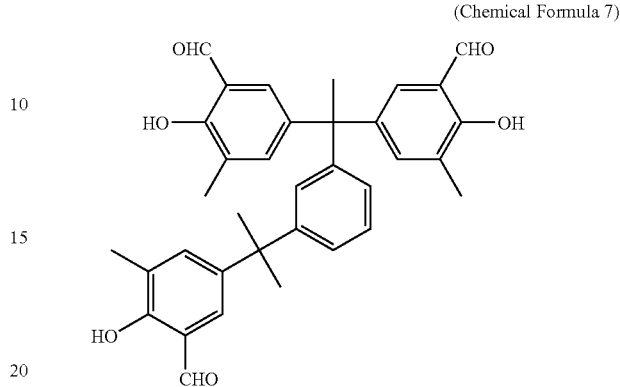

Other examples where the α-(3-formyl-4-hydroxyphenyl)-alkyl group bonds in the para position include, among others, 1-[α-methyl-α-(3-formyl-5-isobutyl-4-hydroxyphenyl)
ethyl]-4-[α,α-bis(3-formyl-5-isobutyl-4-hydroxyphenyl)ethyl]benzene, 1-[α-methyl-α-(3-formyl-5-sec-butyl-4-hydroxyphenyl)
ethyl]-4-[α,α-bis(3-formyl-5-sec-butyl-4-hydroxyphenyl)ethyl]benzene, 1-[α-methyl-α-(3-formyl-5-cyclopentyl-4-hydroxyphenyl)
ethyl]-4-[α,α-bis(3-formyl-5-cyclopentyl-4-hydroxyphenyl)ethyl]benzene, 1-[α-methyl-α-(3-formyl-5-methoxy-4-hydroxyphenyl)
ethyl]-4-[α,α-bis(3-formyl-5-methoxy-4-hydroxyphenyl)ethyl]benzene, 1-[4α-methyl-α-(3-formyl-2,5-dimethyl-4-hydroxyphenyl)
ethyl]-4-[bis(3-formyl-2,5-dimethyl-4-hydroxyphenyl)methyl]benzene, 1-[α-(3-formyl-5-methyl-4-hydroxyphenyl)n-butyl]-4-[α,α-bis(3-formyl-5-methyl-4-hydroxyphenyl)-n-butyl]benzene, and 1-[α-(3-formyl-5-methyl-4-hydroxyphenyl)ethyl]-4-[α,α-bis(3-formyl-5-methyl-4-hydroxyphenyl)ethyl]benzene.

In addition, examples where the α-(3-formyl-4-hydroxyphenyl)-alkyl group bonds in the meta position include, among others, 1-[α-methyl-α-(3-formyl-5-methyl-4-hydroxyphenyl)
ethyl]-3-[α,α-bis(3-formyl-5-methyl-4-hydroxyphenyl)ethyl]benzene, 1-[α-methyl-α-(3-formyl-4-hydroxyphenyl)ethyl]-3-[α,α-bis(3-formyl-4-hydroxyphenyl)ethyl]benzene, 1-[α-methyl-α-(3-formyl-5-ethyl-4-hydroxyphenyl)ethyl]-3-[α,α-bis(3-formyl-5-ethyl-4-hydroxyphenyl)ethyl]benzene, 1-[α-methyl-α-(3-formyl-5-cyclohexyl-4-hydroxyphenyl)
ethyl]-3-[α,α-bis(3-formyl-5-cyclohexyl-4-hydroxyphenyl)ethyl]benzene, 1-[α-methyl-α-(3-formyl-5-t-butyl-4-hydroxyphenyl)
ethyl]-3-[α,α-bis(3-formyl-5-t-butyl-4-hydroxyphenyl)ethyl]benzene, 1-[α-methyl-α-(3-formyl-5-isopropyl-4-hydroxyphenyl)
ethyl]-3-[α,α-bis(3-formyl-5-isopropyl-4-hydroxyphenyl)ethyl]benzene, and 1-[α-(3-formyl-2-methoxy-5-methyl-4-hydroxyphenyl)
ethyl]-3-[bis(3-formyl-2-methoxy-5-methyl-4-hydroxyphenyl)methyl]benzene.

Other examples where the hydroxyl group is in the o-position include, among others, 1-[α-(3-formyl-5-methyl-2-hydroxyphenyl)ethyl]-4-[bis(3-formyl-5-methyl-2-hydroxyphenyl)ethyl]benzene.

If Y is a —$R_2COOR_3$ group in a trisformylphenyl expressed by the aforementioned General Formula (1), then the aforementioned General Formula (1) represents a tris(ether-formylphenyl). A desired tris(ether-formylphenyl) is tris(4-ether-3-formylphenyl), expressed by General Formula (6) specified below.

[Chemical 13]

General Formula (6)

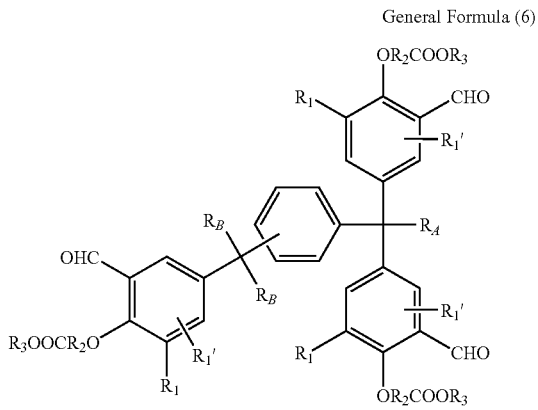

In the formula, $R_1$, $R_A$ and $R_B$ are the same as the items represented by the corresponding symbols in General Formula (1), and $R_1'$ is the same as $R_1$ in General Formula (1). $R_2$ and $R_3$ are the same as the items represented by the corresponding symbols in General Formula (1), where $R_2$ is a monocyclic or condensed cyclic aromatic hydrocarbon group with a carbon atom number of 6 to 15 or an aliphatic hydrocarbon group with a carbon atom number of 1 to 8 that may have in its main chain a monocyclic or condensed cyclic aromatic hydrocarbon group with a carbon atom number of 6 to 15. $R_3$ is a hydrogen atom or alkyl group with a carbon atom number of 1 to 6.

To be specific, $R_1$ and $R_1'$ are respectively a hydrogen atom, alkyl group with a carbon atom number of 1 to 8 or alkoxy group with a carbon atom number of 1 to 8. $R_2$ is a monocyclic or condensed cyclic aromatic hydrocarbon group with a carbon atom number of 6 to 15 or an aliphatic hydrocarbon group with a carbon atom number of 1 to 8 that may have in its main chain a monocyclic or condensed cyclic aromatic hydrocarbon group with a carbon atom number of 6 to 15. $R_3$ is a hydrogen atom or alkyl group with a carbon atom number of 1 to 6. $R_A$ and $R_B$ are respectively a hydrogen atom or alkyl group with a carbon atom number of 1 to 6.

For $R_1$, specific examples of an alkyl group with a carbon atom number of 1 to 8 include, among others, straight- or branched-chain or cyclic alkyl groups such as methyl group, ethyl group, propyl group, butyl group, t-butyl group, pentyl group, 3-methylpentyl group, cyclopropyl group, cyclopentyl group, 3-methylcyclopentyl group, cyclohexyl group, 2,4-dimethylcyclohexyl group and cycloheptyl group. Examples of an alkoxyl group with a carbon atom number of 1 to 8 include, among others, straight- or branched-chain or cyclic alkoxyl groups such as methoxy group, ethoxy group, propoxy group, isopropoxy group, butoxy group, t-butoxy group, pentyloxy group, isopentyloxy group, cyclopropoxy group, cyclopentyloxy group, 3-methylcyclopentyloxy group, cyclohexyloxy group, 2,4-dimethyl cyclohexyloxy group and cycloheptyloxy group. Among the above, straight- or branched-chain alkyl or alkoxyl groups with a carbon atom number of 1 to 4 or cyclic alkyl or cyclic alkoxyl groups with a carbon atom number of 5 to 7 are desirable, of which straight- or branched-chain alkyl groups with a carbon atom number of 1 to 4 are particularly desirable. For $R_1'$, specific examples of an alkyl or alkoxy group with a carbon atom number of 1 to 8 are the same as those of $R_1$, where desirable alkyl groups include, among others, primary or secondary alkyl groups, of which straight- or branched-chain alkyl groups with a carbon atom number of 1 to 4 are desirable, while desirable alkoxy groups include, among others, straight- or branched-chain alkoxy groups with a carbon atom number of 1 to 4. If $R_A$ is an alkyl group, $R_1'$ should desirably be a hydrogen atom. Specific examples and desirable forms of alkyl groups for $R_A$ and $R_B$ are the same as those pertaining to General Formula (2).

Accordingly, a more desirable structure is expressed by General Formula (7) specified below.

[Chemical 14]

General Formula (7)

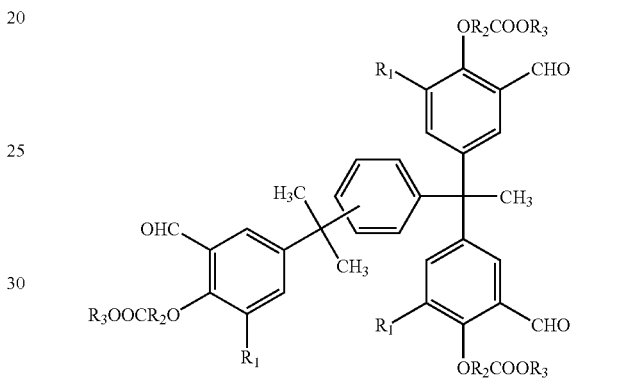

In the formula, $R_1$, $R_2$ and $R_3$ are the same as the items represented by the corresponding symbols in General Formula (6).

Also, in General Formulas (6) and (7), the bonding position with the phenyl nucleus may change to the o-, m- or p-position relative to the bis(3-formyl-4-etherphenyl)alkyl group and the bonding position of the (4-ether-3-formylphenyl)-alkyl group should desirably be the para or meta position.

In the formula, $R_2$ represents a monocyclic or condensed cyclic aromatic hydrocarbon group with a carbon atom number of 6 to 15 or an aliphatic hydrocarbon group with a carbon atom number of 1 to 8 that may have in its main chain a monocyclic or condensed cyclic aromatic hydrocarbon group with a carbon atom number of 6 to 15.

In the aforementioned $R_2$, a desirable carbon atom number is 6 to 10 for a monocyclic or condensed cyclic aromatic hydrocarbon group with a carbon atom number of 6 to 15, where such aromatic hydrocarbon group may be substituted by an alkyl group with a carbon atom number of 1 to 4, and specific examples and favorable forms of this $R_2$ include, among others, 1,2-phenylene, 1,3-phenylene, 1,4-phenylene, 2-methyl-1,4-phenylene, 2,6-dimethyl-1,4-phenylene, 2-isopropyl-1,4-phenylene and other monocyclic aromatic hydrocarbons, and 1,5-naphthylene, 2,7-naphtylene, anthracene-2,7-diyl, fuluorene-2,7-diyl and other condensed cyclic aromatic hydrocarbons.

Also, regarding the aliphatic hydrocarbon group with a carbon atom number of 1 to 8 that may have in its main chain a monocyclic or condensed cyclic aromatic hydrocarbon group with a carbon atom number of 6 to 15 representing the aforementioned $R_2$, bivalent aliphatic hydrocarbons with a carbon atom number of 1 to 8 that do not have any aromatic hydrocarbon group are straight- or branched-chain saturated or unsaturated alkylene groups with a carbon atom number of 1 to 8, where specific examples include, among others, methylene, ethane-1,2-diyl, ethane-1,1-diyl, propylene, propane-1,1-diyl, butylene, ethyl ethylene, 2-methyl-1,3-propylene, 2-methyl butane-1,4-diyl, pentamethylene, hexamethylene, 1,1,2,2-tetramethyl ethylene, isopropyl methylene, 1,1-diethyl-methylene and other saturated alkylene groups, and vinylene, propenylene, 2-butenileyen, 2-pentenylene and other unsaturated alkylene groups, of which aliphatic saturated hydrocarbon groups are desired. Also, regarding the aliphatic hydrocarbon group with a carbon atom number of 1 to 8 that may have in its main chain a monocyclic or condensed cyclic aromatic hydrocarbon group with a carbon atom number of 6 to 15 representing the aforementioned $R_2$, the other form, or aliphatic hydrocarbon group having an aromatic hydrocarbon group, is expressed by the General Formula (15) specified below.

[Chemical 15]

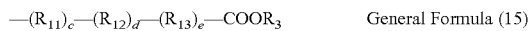

General Formula (15)

In the formula, $R_{11}$ and $R_{13}$ are respectively and independently an aliphatic hydrocarbon group with a carbon atom number of 1 to 8, and c, d and e are respectively 1 or 0, where the total carbon atom number of $R_{11}+R_{13}$ is 1 to 8, not all of c, d and e are 0, and $R_{12}$ represents a monocyclic or condensed cyclic aromatic hydrocarbon group with a carbon atom number of 6 to 15.

In General Formula (15), specific examples of a hydrocarbon group expressed by $R_{11}$ or $R_{13}$ are the same as aliphatic hydrocarbon groups expressed by $R_2$ in General Formula (6), while similarly monocyclic or condensed cyclic aromatic hydrocarbon groups with a carbon atom number of 6 to 15, expressed by $R_{12}$, are the same as monocyclic or condensed cyclic aromatic hydrocarbon groups expressed by $R_2$. Among the above, phenylene and naphthylene groups are desirable for the aromatic hydrocarbon group $R_{12}$, while aliphatic saturated hydrocarbon groups are desirable, and alkylene or alkylidene groups with a carbon atom number of 1 to 4 are more desirable, for the aliphatic hydrocarbon groups $R_{11}$ and $R_{13}$.

Accordingly, specific examples of an aliphatic hydrocarbon group with a carbon atom number of 1 to 8 that may have in its main chain a monocyclic or condensed cyclic aromatic hydrocarbon group with a carbon atom number of 6 to 15 include the following, among others:

[Chemical 16]

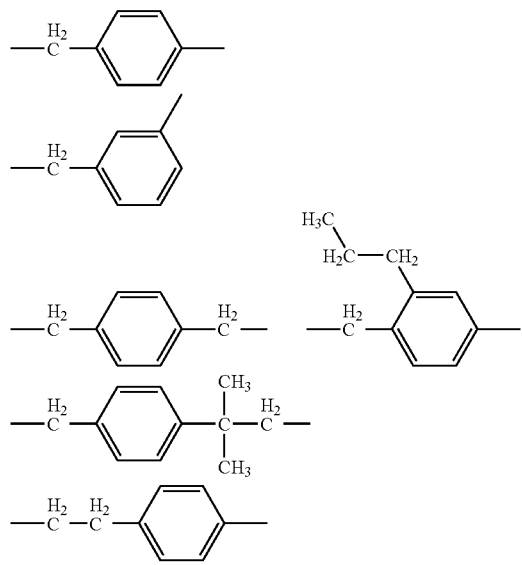

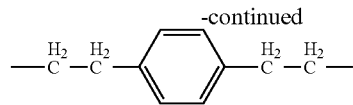

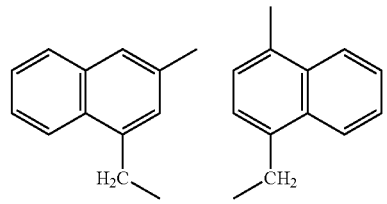

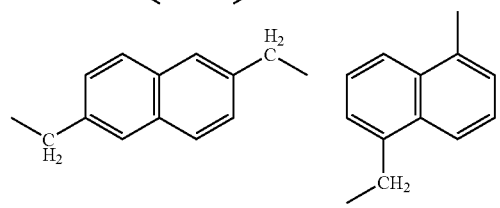

Also, regarding $R_2$ in General Formula (6), the carbon atom bonding with the ether group that bonds with the aromatic nucleus should desirably be a primary or secondary carbon atom for its stability against acid.

On the other hand, $R_3$ represents a hydrogen atom or alkyl group with a carbon atom number of 1 to 6, where said alkyl group with a carbon atom number of 1 to 6 is a straight- or branched-chain alkyl group, and specific examples include, among others, methyl, ethyl, n-butyl, t-butyl, sec-butyl, isopropyl and n-propyl.

Accordingly with a tris(4-ether-3-formylphenyl) expressed by General Formula (6), specific examples of an ester-substituted hydrocarbon group bonding with an ether group, or specifically carboxyhydrocarbon group or alkoxycarbonyl hydrocarbon group represented by —$R_2COOR_3$, include, among others, carboxymethyl group, methoxycarbonylmethyl group, carboxypropyl group, ethoxycarbonylpropyl group, 3-methoxycarbonyl-2-methyl-1-propyl group, methoxycarbonylpropenyl group, and the following:

[Chemical 17]

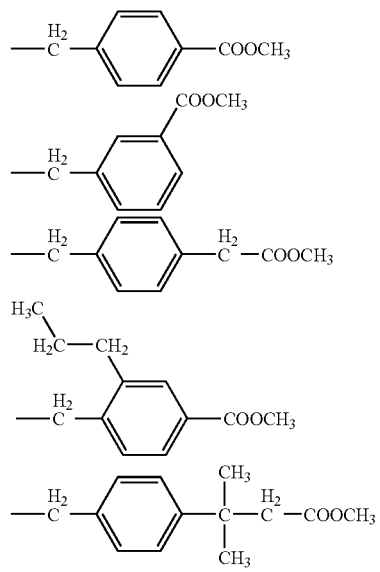

-continued

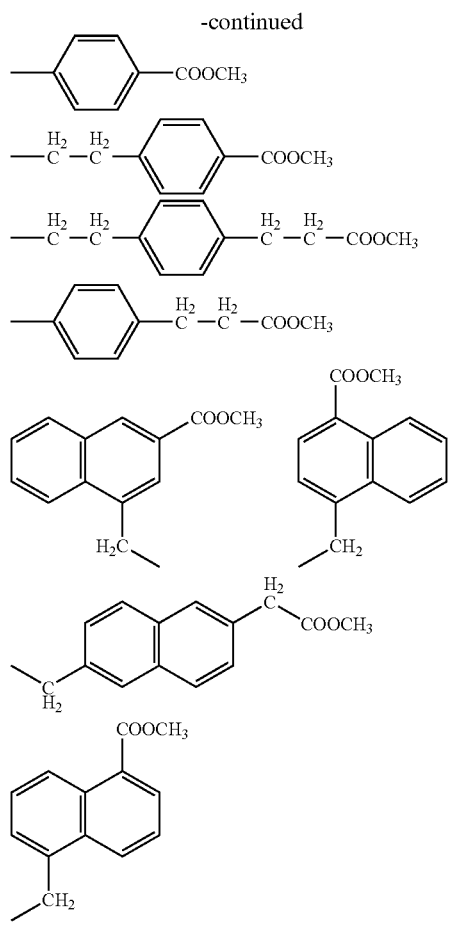

Accordingly, specific examples of a tris(4-ether-3-formylphenyl) expressed by General Formula (6) conforming to the present invention include, among others:

1-[α-methyl-α-(3-formyl-4-methoxycarbonylmethoxy-5-methylphenyl)ethyl]-4-[α,α-bis(3-formyl-4-methoxycarbonylmethoxy-5-methylphenyl)ethyl]benzene (Compound 8);

[Chemical 18]

(Chemical Formula 8)

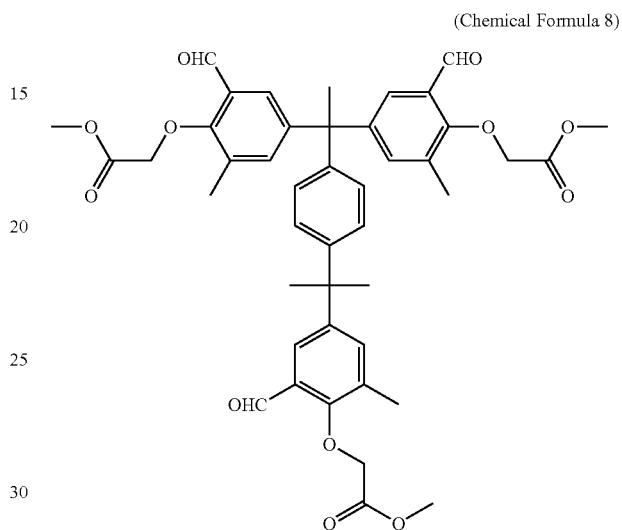

1-[α-methyl-α-(3-formyl-4-(4-methoxycarbonylphenyl)methoxy-5-methylphenyl)ethyl]-4-[α,α-bis(3-formyl-4-(4-methoxycarbonylphenyl)methoxy-5-methylphenyl)ethyl]benzene (Compound 9);

[Chemical 19]

(Chemical Formula 9)

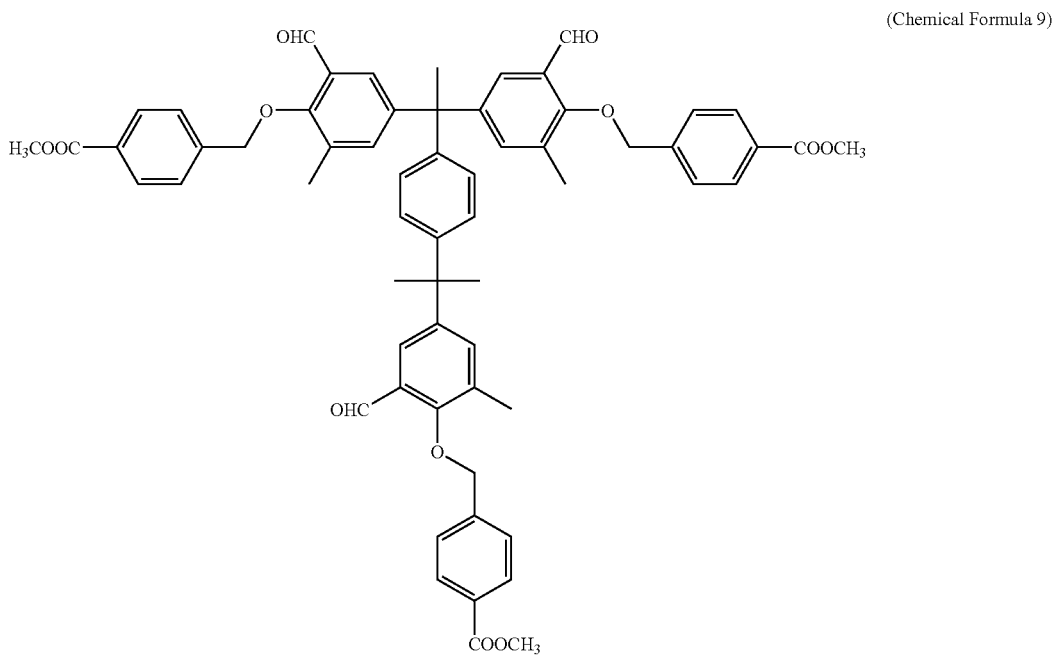

1-[α-methyl-α-(3-formyl-4-(5-methoxycarbonyl-1-naphtyl)methoxy-5-methylphenyl)ethyl]-4-[α,α-bis(3-formyl-4-(5-methoxycarbonyl-1-naphthyl)methoxy-5-methylphenyl)ethyl]benzene (Compound 10); or

[Chemical 20]

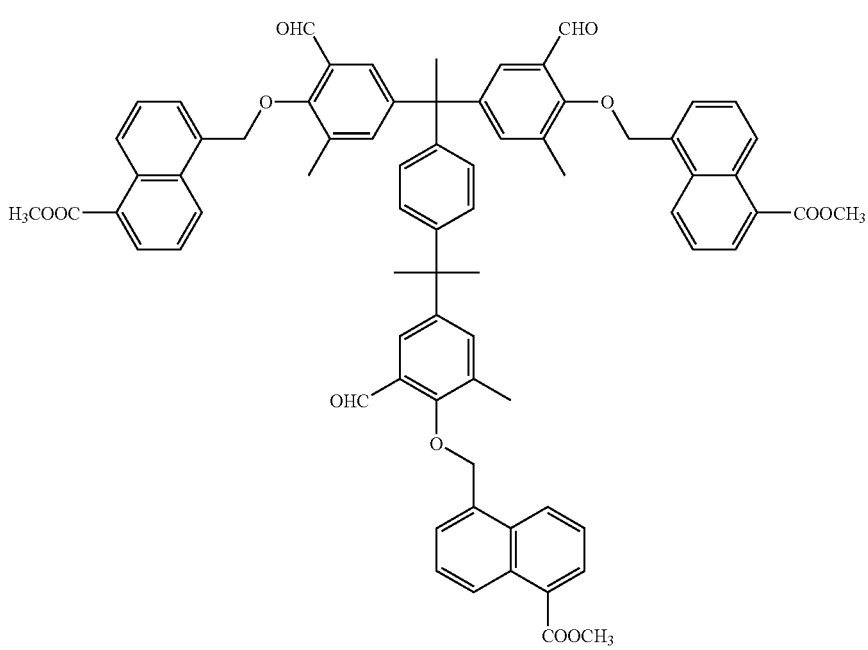

(Chemical Formula 10)

1-[α-methyl-α-(3-formyl-4-carboxymethoxy-5-isopropylphenyl)ethyl]-4-[α,α-bis(3-formyl-4-carboxymethoxy-5-isopropylphenyl)ethyl]benzene, 1-[α-methyl-α-(3-formyl-4-methoxycarbonylmethoxy-5-cyclohexylphenyl)ethyl]-4-[α,α-bis(3-formyl-4-methoxycarbonylmethoxy-5-cyclohexylphenyl)ethyl]benzene, 1-[α-methyl-α-(3-formyl-4-(4-methoxycarbonylphenyl)methoxy-5-isopropylphenyl)ethyl]-4-[α,α-bis(3-formyl-4-(4-methoxycarbonylphenyl)methoxy-5-isopropylphenyl)ethyl]benzene, 1-[α-methyl-α-(3-formyl-4-(4-methoxycarbonylphenyl)methoxy-5-cyclohexylphenyl)ethyl]-4-[α,α-bis(3-formyl-4-(4-methoxycarbonylphenyl)methoxy-5-cyclohexylphenyl)ethyl]benzene, 1-[α-methyl-α-(3-formyl-4-methoxycarbonylmethoxy-5-methoxyphenyl)ethyl]-4-[α,α-bis(3-formyl-4-methoxycarbonylmethoxy-5-methoxyphenyl)ethyl]benzene, 1-[α-methyl-α-(3-formyl-4-t-butoxycarbonylmethoxy-5-methoxyphenyl)ethyl]-4-[α,α-bis(3-formyl-4-t butoxycarbonylmethoxy-5-methoxyphenyl)ethyl]benzene, 1-[α-methyl-α-(3-formyl-4-methoxycarbonylmethoxyphenyl)ethyl]-4-[α,α-bis(3-formyl-4-methoxycarbonylmethoxyphenyl)ethyl]benzene, 1-[α-methyl-α-(3-formyl-4-methoxycarbonylmethoxy-5-methylphenyl)ethyl]-3-[α,α-bis(3-formyl-4-methoxycarbonylmethoxy-5-methylphenyl)ethyl]benzene, 1-[α-methyl-α-(3-formyl-4-methoxycarbonylmethoxy-2,5-dimethylphenyl)ethyl]-4-[bis(3-formyl-4-methoxycarbonylmethoxy-2,5-dimethylphenyl)methyl]benzene, 1-[α-(3-formyl-4-methoxycarbonylmethoxy-5-methylphenyl)n-pentyl]-4-[α,α-bis(3-formyl-4-methoxycarbonylmethoxy-5-methylphenyl)-n-butyl]benzene, 1-[α-(3-formyl-4-methoxycarbonylmethoxy-5-methylphenyl)ethyl]-4-[α,α-bis(3-formyl-4-methoxycarbonylmethoxy-5-methylphenyl)ethyl]benzene, and 1-[α-(3-formyl-2-methoxy-4-methoxycarbonylmethoxy-5-methylphenyl)ethyl]-3-[bis(3-formyl-2-methoxy-4-methoxycarbonylmethoxy-5-methylphenyl)methyl]benzene.

Such tris(formylphenyl) expressed by the aforementioned General Formula (1) conforming to the present invention is not specifically limited in its production method, and a tris(formylphenol) expressed by the aforementioned General Formula (2) where Y is a hydrogen atom in a tris(formylphenyl) expressed by the aforementioned General Formula (1) can be produced by, for example, causing a tris(hydroxymethylphenol) expressed by General Formula (16) specified below, corresponding to the target tris(formylphenol), to react with hexamethylenetetramine in the presence of an acid, and then hydrolyzing the obtained reaction product, as shown by Reaction Formula (1) specified below.

Reaction Formula (1)

[Chemical 21]

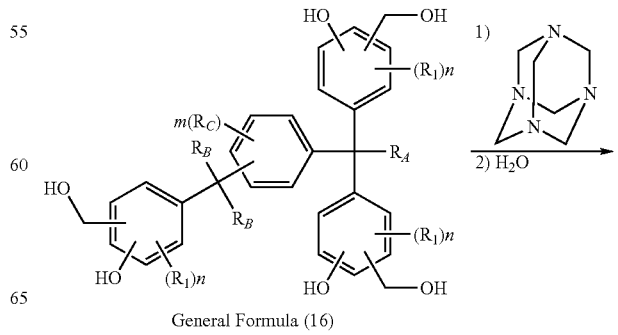

General Formula (16)

-continued

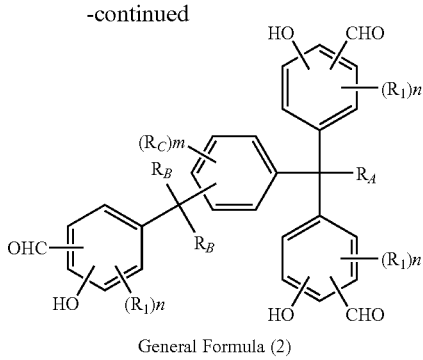

General Formula (2)

In General Formula (16), $R_1$, $R_A$, $R_B$, $R_C$, n and m are the same as the items represented by the corresponding symbols in General Formula (2).

To be more specific, a favorable embodiment of a tris (formylphenol) expressed by General Formula (2), or specifically a tris(formylphenol) expressed by General Formula (5) specified below, can be produced by causing a tris(hydroxymethylphenol) expressed by General Formula (17) specified below, corresponding to the target tris(formylphenol), to react with hexamethylenetetramine in the presence of an acid, and then hydrolyzing the obtained reaction product, as shown by Reaction Formula (2) specified below.

Reaction Formula (2)

[Chemical 22]

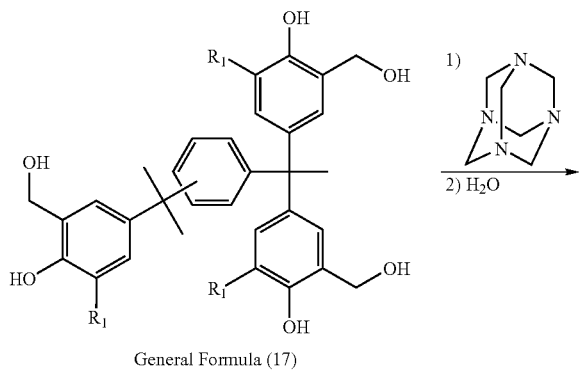

General Formula (17)

General Formula (5)

In General Formula (17), $R_1$ is the same as the item represented by the corresponding symbol in General Formula (5).

Also as another production method, a tris(formylphenol) expressed by General Formula (2) can also be obtained by causing a trisphenol expressed by General Formula (18) specified below, corresponding to the target tris(formylphenol), to reaction with hexamethylenetetramine via a known DUFF reaction in the presence of an acid and then hydrolyzing the obtained reaction product, as shown by Reaction Formula (3) specified below. In General Formula (18), however, at least one of the o- and p-positions of the hydroxyl group is not substituted.

Reaction Formula (3)

[Chemical 23]

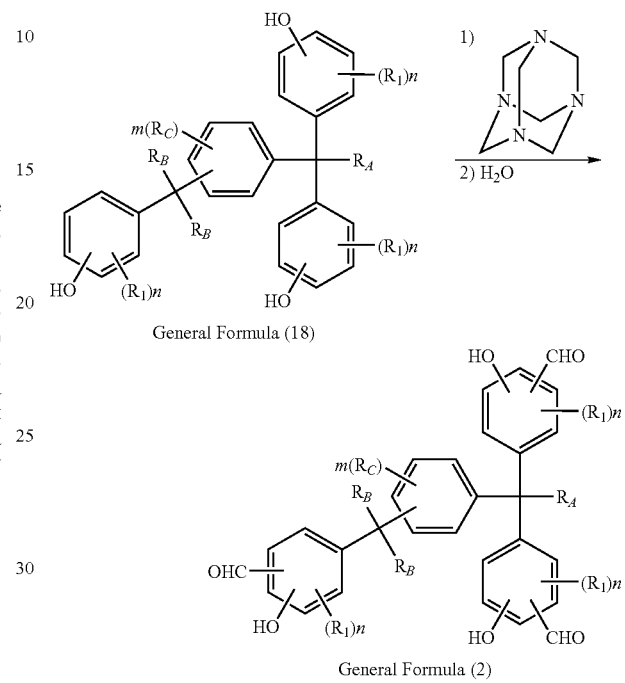

General Formula (18)

General Formula (2)

In General Formula (18), $R_1$, $R_A$, $R_B$, $R_C$, n and m are the same as the items represented by the corresponding symbols in General Formula (2).

To be more specific, a favorable embodiment of a tris (formylphenol) expressed by General Formula (2), or specifically a tris(formylphenol) expressed by General Formula (5) specified below, can be produced by, for example, causing a trisphenol expressed by General Formula (19) specified below, corresponding to the target tris(formylphenol), to react with hexamethylenetetramine via a known DUFF reaction in the presence of an acid, and then hydrolyzing the obtained reaction product, as shown by Reaction Formula (4) specified below.

Reaction Formula (4)

[Chemical 24]

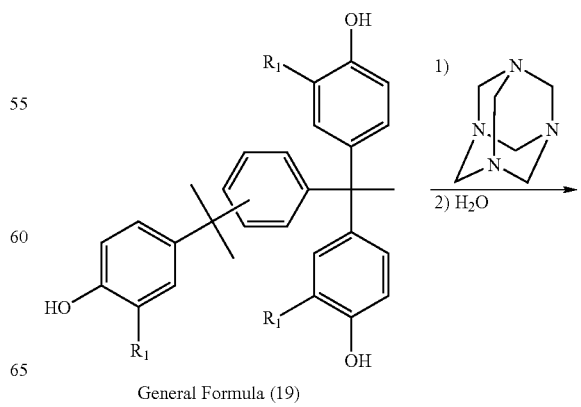

General Formula (19)

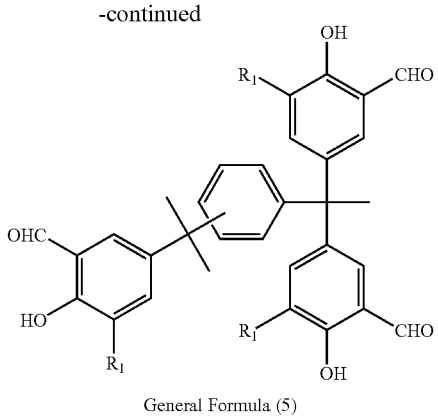

General Formula (5)

In General Formula (19), $R_1$ is the same as the item represented by the corresponding symbol in General Formula (5).

However, the methods using these Reaction Formulas (3) and (4) provide low yields and generate many byproducts, which makes refining difficult. Accordingly, the methods using the aforementioned Reaction Formulas (1) and (2) are desirable.

In the aforementioned Reaction Formulas (1) and (2), $R_1$, $R_A$, $R_B$, $R_C$, n and m in the formula representing the material tris(hydroxymethylphenol) expressed by the aforementioned General Formula (16) or (17) are the same as the items represented by the corresponding symbols in General Formula (2), and therefore specific examples of a tris(hydroxymethylphenol) expressed by the aforementioned General Formula (16) or (17) include, among others, 1-[α-methyl-α-(3-hydroxymethyl-5-methyl-4-hydroxyphenyl)ethyl]-4-[α,α-bis(3-hydroxymethyl-5-methyl-4-hydroxyphenyl)ethyl]benzene as a material for 1-[α-methyl-α-(3-formyl-5-methyl-4-hydroxyphenyl)ethyl]-4-[α,α-bis(3-formyl-5-methyl-4-hydroxyphenyl)ethyl]benzene (Compound 1), 1-[α-methyl-α-(3-hydroxymethyl-4-hydroxyphenyl)ethyl]-4-[α,α-bis(3-hydroxymethyl-4-hydroxyphenyl)ethyl]benzene as a material for 1-[α-methyl-α-(3-formyl-4-hydroxyphenyl)ethyl]-4-[α,α-bis(3-formyl-4-hydroxyphenyl)ethyl]benzene (Compound 2), 1-[α-methyl-α-(3-hydroxymethyl-5-ethyl-4-hydroxyphenyl)ethyl]-4-[α,α-bis(3-hydroxymethyl-5-ethyl-4-hydroxyphenyl)ethyl]benzene as a material for 1-[α-methyl-α-(3-formyl-5-ethyl-4-hydroxyphenyl)ethyl]-4-[α,α-bis(3-formyl-5-ethyl-4-hydroxyphenyl)ethyl]benzene (Compound 3), 1-[α-methyl-α-(3-hydroxymethyl-5-cyclohexyl-4-hydroxyphenyl)ethyl]-4-[α,α-bis(3-hydroxymethyl-5-cyclohexyl-4-hydroxyphenyl)ethyl]benzene as a material for 1-[α-methyl-α-(3-formyl-5-cyclohexyl-4-hydroxyphenyl)ethyl]-4-[α,α-bis(3-formyl-5-cyclohexyl-4-hydroxyphenyl)ethyl]benzene (Compound 4), 1-[α-methyl-α-(3-hydroxymethyl-5-t-butyl-4-hydroxyphenyl)ethyl]-4-[α,α-bis(3-hydroxymethyl-5-t-butyl-4-hydroxyphenyl)ethyl]benzene as a material for 1-[α-methyl-α-(3-formyl-5-t-butyl-4-hydroxyphenyl)ethyl]-4-[α,α-bis(3-formyl-5-t-butyl-4-hydroxyphenyl)ethyl]benzene (Compound 5), 1-[α-methyl-α-(3-hydroxymethyl-5-isopropyl-4-hydroxyphenyl)ethyl]-4-[α,α-bis(3-hydroxymethyl-5-isopropyl-4-hydroxyphenyl)ethyl]benzene as a material for 1-[α-methyl-α-(3-formyl-5-isopropyl-4-hydroxyphenyl)ethyl]-4-[α,α-bis(3-formyl-5-isopropyl-4-hydroxyphenyl)ethyl]benzene (Compound 6), 1-[α-methyl-α-(3-hydroxymethyl-5-methyl-4-hydroxyphenyl)ethyl]-3-[α,α-bis(3-hydroxymethyl-5-methyl-4-hydroxyphenyl)ethyl]benzene as a material for 1-[α-methyl-α-(3-formyl-5-methyl-4-hydroxyphenyl)ethyl]-3-[α,α-bis(3-formyl-5-methyl-4-hydroxyphenyl)ethyl]benzene (Compound 7), and 1-[α-(3-hydroxymethyl-5-methyl-4-hydroxyphenyl)n-butyl]-4-[α,α-bis(3-hydroxymethyl-5-methyl-4-hydroxyphenyl)-n-butyl]benzene as a material for 1-[α-(3-formyl-5-methyl-4-hydroxyphenyl)n-butyl]-4-[α,α-bis(3-formyl-5-methyl-4-hydroxy phenyl)n-butyl]benzene.

When such trishydroxymethylphenol expressed by the aforementioned General Formula (16) or (17) is caused to react with hexamethylenetetramine in the presence of an acid in a production method expressed by the aforementioned Reaction Formula (1) or (2), favorable examples of acids that can be used include, among others, acetic acid, formic acid, trifluoroacetic acid, oxalic acid, benzoic acid, fluorobenzoioc acid and other organic carbonic acids, trifluoroacetic acid, trichloroacetic acid, tribromoacetic acid, monofluoroacetic acid, monochloroacetic acid and other halogenated organic carbonic acids, and boric acid and other inorganic weak acids.

Among the above, organic carbonic acids are more desirable, and trifluoroacetic acid is especially desirable.

The amount of acid used in the reaction varies according to the type of acid in terms of the range of added amount or optimal amount of acid. With trifluoroacetic acid, for example, the range is approx. 2 to 50 mols, or desirably approx. 10 to 30 mols, relative to 1 mol of trishydroxymethylphenol.

The form of hexamethylenetetramine is not specially limited, and a hexamethylenetetramine produced by adding to the reaction system ammonia and formaldehyde, both of which are materials for hexamethylenetetramine, may be used, for example.

The amount of hexamethylenetetramine should normally be in a range of 3 to 6 mols, or more desirably in a range of 3.1 to 4.5 mols, relative to 1 mol of trishydroxymethylphenol.

A solvent is not specifically needed in the reaction, as long as the reaction materials can be dissolved and the reaction composition can be agitated. If the melting point of the acid or any material used is high, the reaction liquid has high viscosity at the reaction temperature, or otherwise agitation becomes difficult, it is desirable to use a solvent.

Any solvent can be used as long as it does not inhibit the reaction. Examples include, among others, diethyl ether, tetrahydrofuran and other aliphatic ethers, methanol, cyclohexanol and other aliphatic alcohols, toluene, xylene and other aromatic hydrocarbons, and mixtures thereof.

It is desirable to use acetic acid or trifluoroacetic acid, because these acids also function as solvents.

The method and order in which the reaction materials are input are not limited, and any desired method or order can be selected as deemed appropriate according to the physical properties of the materials used, etc. If an organic carbonic acid is used, for example, it is desirable to add the material trishydroxymethylphenol to a solution where the organic carbonic acid, hexamethylenetetramine and solvent may coexist.

The reaction temperature and pressure are not specifically limited, as long as the reaction can progress smoothly. However, the reaction temperature should normally be in a range of −50 to 150° C., or desirably in a range of 50 to 90° C., while the reaction pressure should normally be in a range of slight decompression to slight pressurization, or preferably around a normal pressure.

Under the production method expressed by Reaction Formula (1), the target tris(formylphenol) is obtained by causing the aforementioned tris(hydroxymethylphenol) to react with hexamethylenetetramine in the presence of an acid and then hydrolyzing the obtained intermediate reaction product.

In the hydrolysis reaction, the intermediate reaction product obtained from the reaction with hexamethylenetetramine may be separated by filtering, etc., or further refined as necessary. From the viewpoints of reaction efficiency, improved yield, etc., however, it is desirable to directly use the mixture obtained from the aforementioned reaction with hexamethylenetetramine. A catalyst may or may not be used in the reaction, but it is desirable to use a catalyst. The catalyst used may be an acid or alkali catalysts, where examples of acid catalysts include, among others, hydrochloric acid, sulfuric acid and other mineral acids, p-toluene sulfonic acid and other organic sulfonic acids, phosphoric acid, or acetic acid, formic acid, trifluoroacetic acid and other organic carbonic acids. Examples of alkali acids include, among others, sodium hydroxide and tetramethylammoniumhydroxide. It is also possible to directly use the acid used in the reaction with hexamethylenetetramine, as the catalyst for hydrolysis. In this case, more acid may be added if the reaction is slow.

The amount of acid to be used is normally in a range of 0.1 to 100 mols relative to 1 mol of tris(hydroxymethylphenol).

In the hydrolysis reaction, the amount of water in the reaction composition is not specifically limited as long as the reaction can progress smoothly. From the viewpoint of reaction efficiency, etc., normally the amount of water is 3 to 120 mols relative to 1 mol of the material hydroxymethylphenol.

The reaction temperature and pressure are not specifically limited, as long as the reaction can progress smoothly. However, the reaction temperature should normally be in a range of 0 to 100° C., or desirably in a range of 50 to 80° C., while the reaction pressure should normally be in a range of slight decompression to slight pressurization, or preferably around a normal pressure.

After the reaction, the target crude product or refined product can be obtained at high yield using any known method from the mixture obtained from the reaction. If the target substance in the mixture obtained from the reaction has precipitated as crystal, for example, the target substance may be directly filtered out. If it has not precipitated as crystal, a poor solvent may be added to the mixture obtained from the reaction to precipitate and separate the target substance.

If an acid catalyst is used, for example, it is possible to add to the mixture obtained from the reaction an appropriate amount of aqueous sodium hydroxide solution or other alkali water needed to neutralize the acid catalyst to a pH of approx. 4 to 7, and then perform the aforementioned operation to separate/precipitate the target substance, such as adding toluene, methyl isobutyl ketone, ethyl ester acetate, ether or other solvent that can be separated from water to separate the oil layer containing the target substance from the water layer.

After this operation, if necessary in order to refine the target substance the obtained target crude product is mixed with water and toluene, xylene, methyl isobutylketone, ether or other solvent that can be separated from water to dissolve the target substance and then separate the water layer, while washing the oil layer, to obtain the oil layer containing the target substance. Next, the solvent is distilled away from the obtained oil layer, and then a crystallization solvent is added to crystallize and filter out the target substance as coarse crystal. If the purity of the coarse crystal is low, the aforementioned recrystallization operation can be repeated once or multiple times, as necessary.

Under the production method expressed by Reaction Formula (1), the production method for the direct material tris (hydroxymethylphenol) expressed by General Formula (16) or General formula (16') specified below is not specifically limited. However, a tris(formylphenol) expressed by General Formula (2) can be easily obtained from a trisphenol expressed by General Formula (20) or (20') using, for example, the hydroxymethylation reaction described in Japanese Patent Laid-open No. 2003-300922, as shown in Reaction Formula (5) or (5') specified below. Take note that in General Formula (20), at least one of the o- and p-positions of the hydroxyl group is not substituted, while in General Formula (20') at least one o-position of the hydroxyl group is not substituted.

Reaction Formula (5)

[Chemical 25]

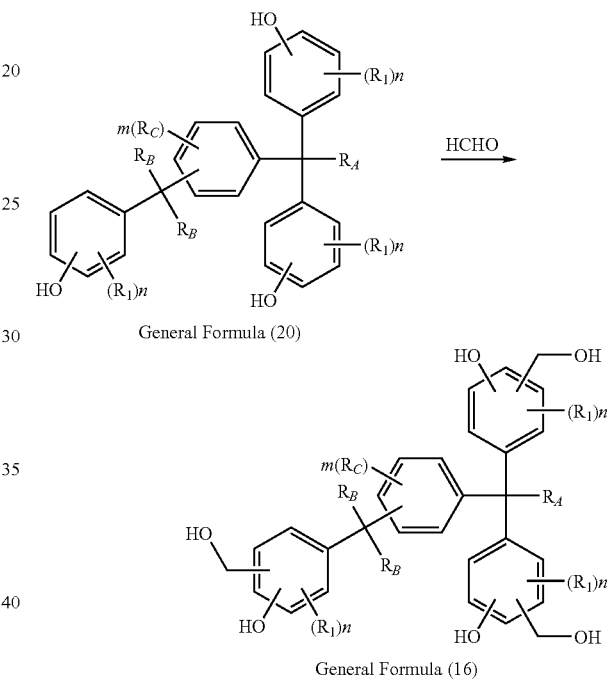

In General Formula (20), $R_1$, $R_A$, $R_B$, $R_C$, n and m are the same as the items represented by the corresponding symbols in General Formula (2).

Reaction Formula (5')

[Chemical 26]

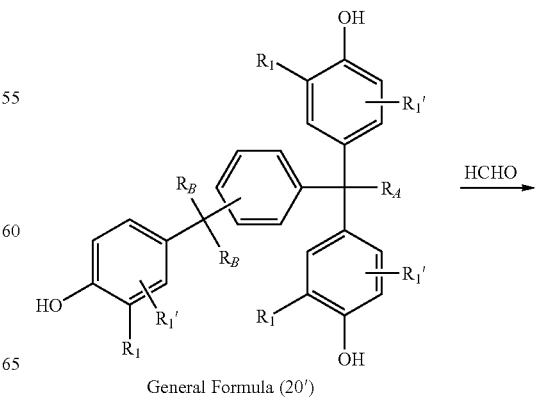

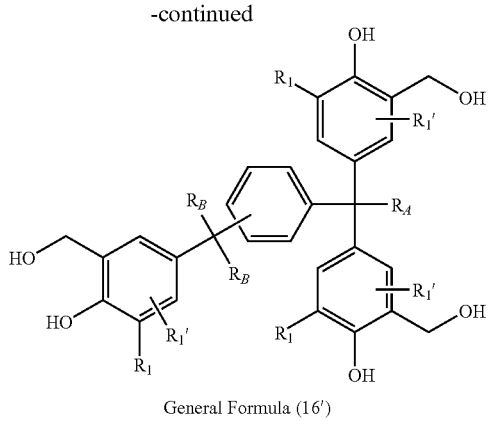

General Formula (16')

In General Formulas (20') and (16'), $R_1$, $R_A$ and $R_B$ are the same as the items represented by the corresponding symbols in General Formula (2), while $R_1'$ is the same as $R_1$ in General Formula (2).

Similarly, a tris(formylphenol) expressed by General Formula (17) can be easily obtained from a trisphenol expressed by General Formula (19) by using, for example, the hydroxymethylation reaction described in Japanese Patent Laid-open No. 2003-300922, as shown in Reaction Formula (6) specified below.

Reaction Formula (6)

[Chemical 27]

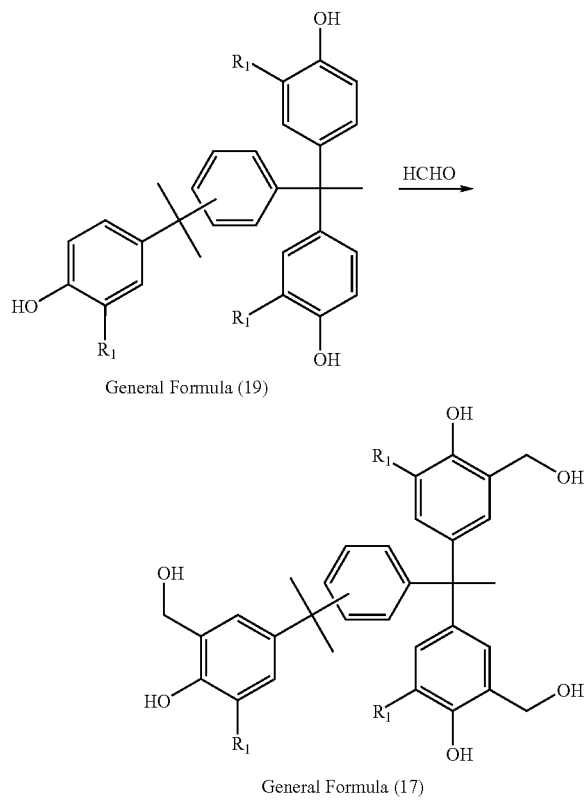

General Formula (19)

General Formula (17)

In General Formula (19), $R_1$ is the same as the item represented by the corresponding symbol in General Formula (2).

Also, a compound according to General Formula (20) or (20') included in the aforementioned Reaction Formula (5) can be obtained by, for example, causing a substituted phenol according to General Formula (21) to react with acyl group-substituted styrene according to General Formula (22) in the presence of an acid catalyst, and also using alkyl mercaptan as an auxiliary catalyst if necessary, without using any solvent or in an alcohol solvent under the conditions described in Japanese Patent Laid-open Nos. Hei 10-101605 or Sho 62-084035, etc., as shown in Reaction Formula (7) specified below.

Reaction Formula (7)

[Chemical 28]

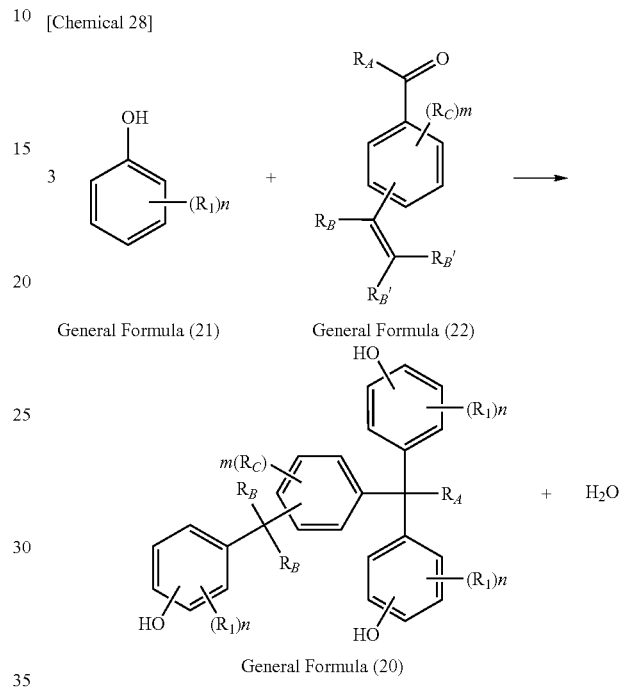

General Formula (21)   General Formula (22)

General Formula (20)

In General Formulas (21) and (22), $R_1$, $R_A$, $R_B$, $R_C$, n and m are the same as the items represented by the corresponding symbols in General Formula (2), while $R_B'$ represents a hydrogen atom or alkyl group with a carbon atom number of 1 to 5, where the total carbon atom number of both $R_B$'s is 5 or less.

In the substituted phenol according to General Formula (21) in the aforementioned Reaction Formula (7), at least two of the o- and p-positions of the hydroxyl group are not substituted. A compound according to General Formula (20) can also be obtained by causing a substituted phenol according to General Formula (21) to react with 1-hydroxyalkyl-acyl benzene according to General Formula (23) in the presence of an acid catalyst under conditions similar to those of Reaction Formula (7), as shown in Reaction Formula (8) specified below.

Reaction Formula (8)

[Chemical 29]

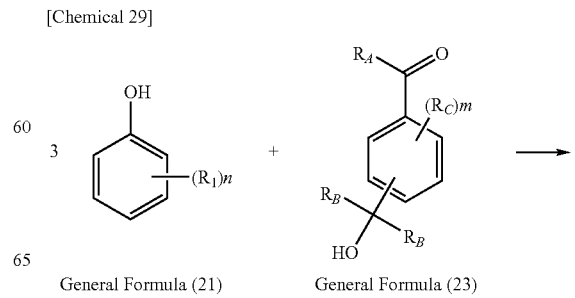

General Formula (21)   General Formula (23)

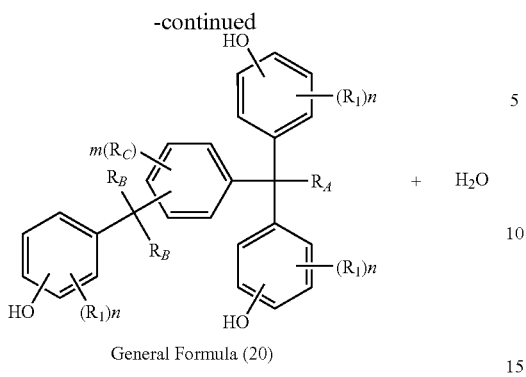

General Formula (20)

In General Formulas (21) and (23), $R_1$, $R_A$, $R_B$, $R_C$, n and m are the same as the items represented by the corresponding symbols in General Formula (2).

Regarding the substituted phenol according to General Formula (21) in the aforementioned Reaction Formula (8), at least two of the o- and p-positions of the hydroxyl group are not substituted.

If $R_A$ in General Formula (22) or (23) is an alkyl group, n in General Formula (21) is 0 or 1, and if n is 1, it is desirable that the substitution position be the o-position of the hydroxyl group.

Also, with a tris(4-ether-3-formylphenyl) expressed by the aforementioned General Formula (6), corresponding to a tris-formylphenol expressed by the aforementioned General Formula (1) where Y is a —$R_2COOR_3$ group, its production method is not specifically limited. For example, a tris(4-ether-3-formylphenol) expressed by the aforementioned General Formula (6) conforming to the present invention can be obtained by causing a tris(3-hydroxymethyl-4-hydroxyphenyl) expressed by the aforementioned General Formula (16') specified below, corresponding to the target tris(4-ether-3-formylphenol), to react with hexamethylenetetramine in the presence of an acid and hydrolyzing the obtained reaction product, as shown by Reaction Formula (9) specified below, and then causing the obtained tris(3-formyl-4-hydroxyphenyl) expressed by the aforementioned General Formula (4), used as a direct material, to react with, say, a halogenated alkoxycarbonyl hydrocarbon expressed by General Formula (24) specified below using any known phenyl ether production method in the presence of a base, as shown in Reaction Formula (10) specified below.

Reaction Formula (9)

[Chemical 30]

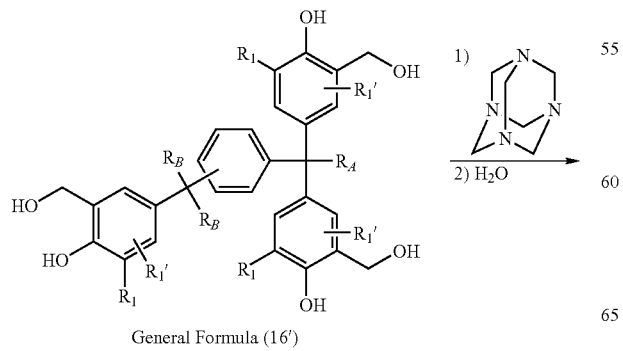

General Formula (16')

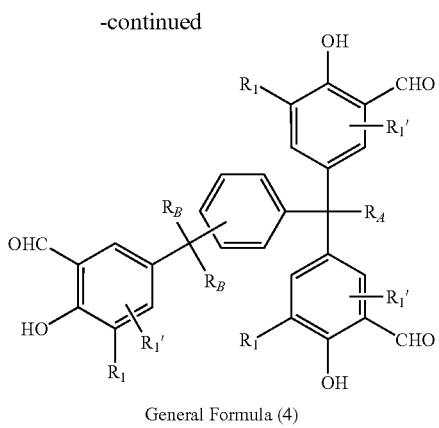

General Formula (4)

[Chemical 31]

Z—$R_2COOR_3$    General Formula (24)

In the formula, Z represents a halogen atom, while $R_2$ and $R_3$ are the same as the items represented by the corresponding symbols in General Formula (6). The halogen atom should desirably be a chlorine atom or bromine atom.

Reaction Formula (10)

[Chemical 32]

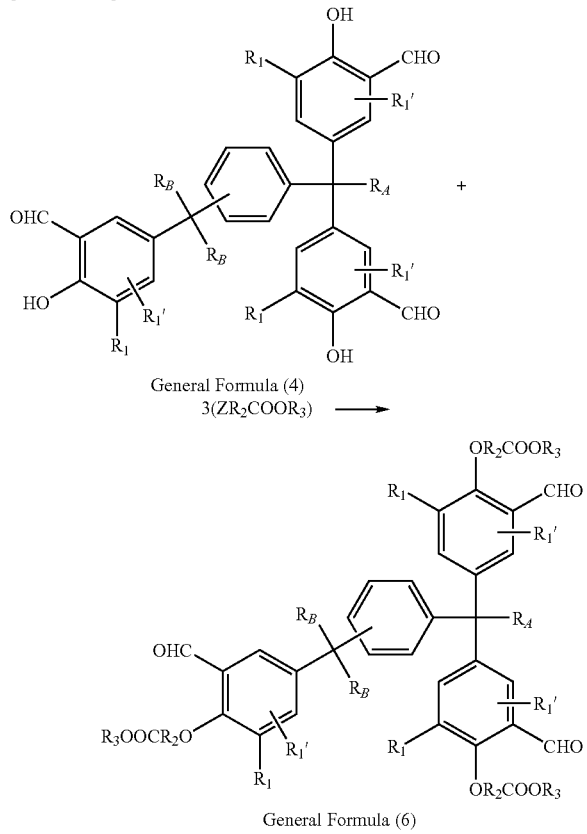

General Formula (6)

To be more specific, an example is shown in Reaction Formula (11) specified below where
1-[α-methyl-α-(3-formyl-5-methyl-4-methoxycarbonyl-methoxyphenyl)ethyl]-4-[α,α-bis(3-formyl-5-methyl-4- methoxycarbonylmethoxyphenyl)ethyl]benzene is obtained from a tris(3-formyl-4-hydroxyphenyl) being 1-[α-methyl-α-(3-formyl-5-methyl-4-hydroxyphenyl)ethyl]-4-[α,α-bis(3-formyl-5-methyl-4-hydroxyphenyl)ethyl]benzene, by using chlorinated methyl ester acetate as a halogenated alkoxycarbonyl hydrocarbon.

Reaction Formula (11)

[Chemical 33]

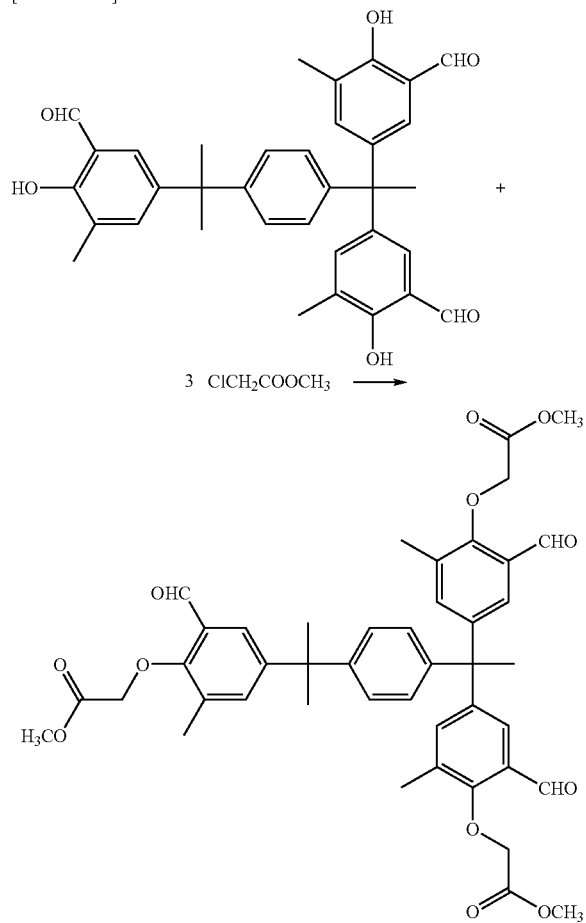

In the production method illustrated by Reaction Formula (10) or (11), a tris(4-hydroxy-3-formylphenyl) is caused to react with a halogenated alkoxycarbonyl hydrocarbon in a reaction solvent, such as dimethylformamide, in the presence of a base such as potassium carbonate.

The base that can be used may be either an organic base or inorganic base. Favorable examples of organic bases include, among others, tetramethylammoniumhydroxide and other quaternary hydroxyamines, and 1,8-diazabicyclo[5.4.0]undec-7-ene (abbreviated as "DBU"). Also, favorable examples of inorganic bases include, among others, sodium hydroxide, potassium hydroxide and other alkali metal hydroxides, potassium carbonate, sodium carbonate and other alkali metal carbonates, hydrogenated sodium, hydrogenated potassium, hydrogenated lithium and other hydrogenated alkali metals, t-butoxy potassium and other alkoxy alkali metals.

The amount of such base to be added should normally be in a range of 3 to 4 mols, or desirably in a range of 3.3 to 3.7 mols, relative to 1 mol of the tris(3-formyl-4-hydroxyphenyl) expressed by General Formula (4).

Favorable examples of solvents used in the reaction include, among others, dioxane, THF and other ethers, dimethylformamide, dimethylacetoamide and other amides, dimethylsulfoxide, hexamethylenephosphonicamide, pyridine, 4-methylpyridine, N-methylpyrrolidone and other amines, or mixtures thereof.

The amount of solvent to be used should normally be in a range of 1 to 10 parts by weight, or desirably in a range of 2 to 5 parts by weight, relative to 1 part by weight of the material tris(3-formyl-4-hydroxyphenyl) from the viewpoint of volumetric ratio of reaction, etc.

Also to promote the etherification reaction, a reaction promoter may be added as necessary, such as iodinated potassium or other iodinated alkali metal, copper, chlorinated copper or other copper compound, or phase transfer catalyst, etc.

In the reaction, the method and order in which the reaction materials are introduced are not limited. However, normally a desirable method is to mix a tris(3-formyl-4-hydroxyphenyl) expressed by General Formula (4) with a base to create an oxy salt, and then add to the mixture liquid a halogenated alkoxycarbonyl hydrocarbon expressed by General Formula (24) to achieve favorable yields.

The reaction should be performed for several hours, such as 2 to 20 hours, at a temperature normally in range of 20 to 200° C., or desirably in a range of 50 to 120° C. The reaction pressure should normally be in a range of slight decompression to slight pressurization, or preferably around a normal pressure.

After the reaction, appropriate amounts of water and an organic solvent such as toluene or cyclohexane are added to the reaction mixture to perform washing and separation, and if necessary, the organic layer is washed and neutralized with an aqueous acid solution to distill out the solvent from the organic layer, after which the residue is mixed with methanol or other aliphatic lower alcohol and, if necessary, toluene or other aromatic hydrocarbon or methyl ethyl ketone or other aliphatic ketone is added to achieve crystallization or filtering, or such washing solvent is distilled out to obtain the target tris(4-ether-3-formylphenyl) expressed by General Formula (6).

Also with a tris(4-ether-3-formylphenyl) expressed by General Formula (6) where $R_3$ is a hydrogen atom, the production method for the carboxyhydrocarbonoxy substituent is not specifically limited. However, a carboxyhydrocarbon group (—$R_2$COOH) substituent can be easily obtained by, for example, hydrolyzing without using any solvent or in a solvent in the presence of an alkali an alkoxycarbonyl hydrocarbon group (—$R_2$COOR$_3$) substituent which is a tris(4-ether-3-formylphenyl) obtained above where $R_3$ is a primary or secondary alkyl group.

For example,

1-[α-methyl-α-(3-formyl-5-methyl-4-carboxymethoxyphenyl)ethyl]-4-[α,α-bis(3-formyl-5-methyl-4-carboxymethoxyphenyl)ethyl]benzene can be obtained by hydrolyzing without using any solvent or in a solvent in the presence of an alkali a 1-[α-methyl-α-(3-formyl-5-methyl-4-methoxycarbonylmethoxyphenyl)ethyl]-4-[α,α-bis(3-formyl-5-methyl-4-methoxycarbonylmethoxyphenyl)ethyl]benzene obtained by the aforementioned Reaction Formula (11), as shown in Reaction Formula (12) specified below.

Reaction Formula (12)

[Chemical 34]

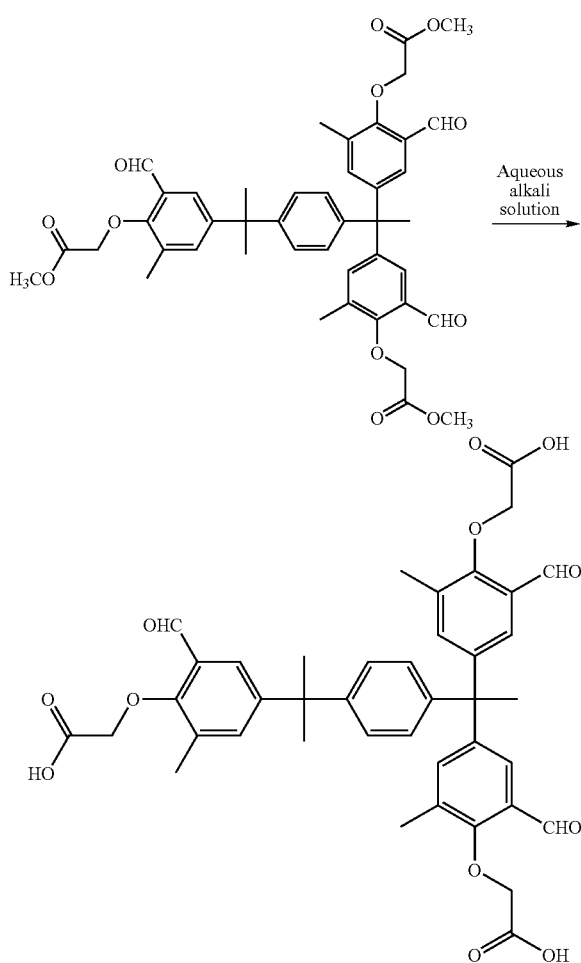

Regarding the production method for a tris(4-ether-3-formylphenyl) where the carboxyhydrocarbon group is obtained by hydrolyzing an alkoxycarbonyl hydrocarbon group (alkoxycarbonylalkyl or alkoxycarbonylaryl group) bonding with the ether group of a tris(4-ether-3-formylphenyl) compound illustrated by the aforementioned Reaction Formula (12), the hydrolysis reaction of the alkoxycarbonyl hydrocarbon group (—$R_2COOR_3$) of the tris(4-ether-3-formylphenyl) can be achieved easily when, as in any known hydrolysis reaction of ester groups, $R_3$ being a primary or secondary alkyl group in the substitution group is a primary alkyl group, and therefore it is preferable.

Accordingly, a carboxyhydrocarbon substituent can be obtained easily by hydrolyzing such tris(4-ether-3-formylphenyl) using an aqueous alkali solution such as sodium hydroxide or tetramethylammonium hydroxide.

As for aqueous alkali solutions that can be used in the hydrolysis reaction, sodium hydroxide, potassium hydroxide and other inorganic strong aqueous alkali solutions or tetramethylammonium hydroxide and other organic strong aqueous alkali solutions are desirable, where the alkali concentration should be in a range of 5 to 50%, or preferably in a range of 10 to 30%. The amount of alkali used should normally be in a range of 3 to 9 mols, or desirably in a range of 3 to 6 mols, relative to 1 mol of the material tris(4-ether-3-formylphenyl).

The reaction temperature should normally be in a range of 0 to 100° C., or desirably in a range of 20 to 60° C. Under such reaction conditions, the reaction is normally ended in approx. 0.5 to 10 hours.

After the reaction, the reaction product may be refined, or a high-purity product may be obtained, if necessary, according to any know method.

Next, another novel compound, or polynuclear polyphenol, under the present invention derived from a tris (formylphenyl) expressed by the aforementioned General Formula (1) is expressed by General Formula (8) specified below.

[Chemical 35]

General Formula (8)

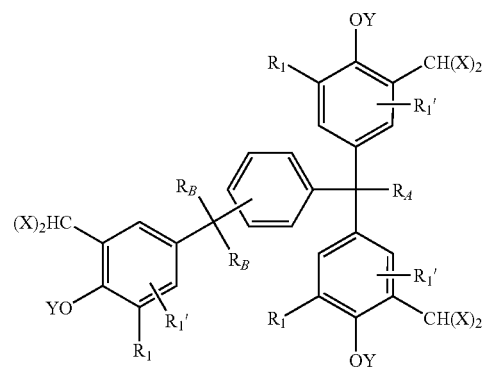

In the formula, $R_1$, $R_A$ and $R_B$ are the same as the items represented by the corresponding symbols in General Formula (1). Y represents a hydrogen atom or —$R_2COOR_3$ group. $R_2$ represents a monocyclic or condensed cyclic aromatic hydrocarbon group with a carbon atom number of 6 to 15 or an aliphatic hydrocarbon group with a carbon atom number of 1 to 8 that may have in its main chain a monocyclic or condensed cyclic aromatic hydrocarbon group with a carbon atom number of 6 to 15. $R_3$ represents a hydrogen atom or primary or secondary alkyl group with a carbon atom number of 1 to 6. X represents a hydroxyphenyl group expressed by General Formula (9) specified below. $R_1'$ is the same as $R_1$ in General Formula (1) and represents a hydrogen atom, alkyl group with a carbon atom number of 1 to 8 or alkoxyl group with a carbon atom number of 1 to 8.

[Chemical 36]

General Formula (9)

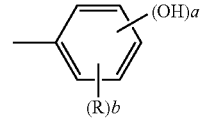

In the formula, R represents a hydrogen atom, alkyl group with a carbon atom number of 1 to 8 or alkoxyl group with a carbon atom number of 1 to 8, while a indicates an integer of 1 to 3 and b indicates an integer of 0 to 4, where 1≦a+b≦5 and if b is 2 or more, Rs may be the same or different.

Also, the substitution position of the group bonded by $R_B$ in a trisformylphenyl group according to the aforementioned General Formula (8) should desirably be the para or meta position relative to the $R_A$-bonded group. A hydroxyphenyl group expressed by General Formula (10) specified below is a favorable example of the aforementioned General Formula (9).

[Chemical 37]

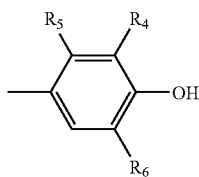

General Formula (10)

In the formula, $R_4$, $R_5$ and $R_6$ are the same as R in General Formula (9). Also, if Y is a hydrogen atom in a trisformylphenyl expressed by the aforementioned General Formula (8), the aforementioned General Formula (8) represents a polynuclear phenol expressed by General Formula (11) specified below.

[Chemical 38]

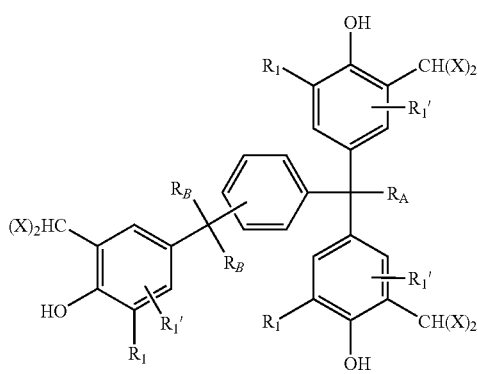

General Formula (11)

In the formula, $R_1$, $R_1'$, $R_A$, $R_B$ and X are the same as the items represented by the corresponding symbols in the aforementioned General Formula (8). Favorable examples of X are the same as those pertaining to the aforementioned General Formula (10).

A polynuclear phenol expressed by General Formula (12) specified below is a favorable example of a polynuclear phenol expressed by the aforementioned General Formula (11) where $R_1'$ is a hydrogen atom and $R_A$ and $R_B$ are methyl groups.

[Chemical 39]

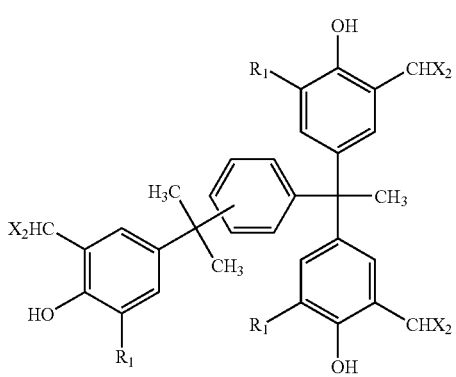

General Formula (12)

In the formula, $R_1$ and X are the same as the items represented by the corresponding symbols in General Formula (8). Favorable examples of X are the same as those pertaining to the aforementioned General Formula (10).

In the aforementioned General Formulas (9) and (10), R, $R_4$, $R_5$ and $R_6$ respectively indicate a hydrogen atom, alkyl group with a carbon atom number of 1 to 8 or alkoxyl group with a carbon atom number of 1 to 8, where specific examples of an alkyl group with a carbon atom number of 1 to 8 are the same as those of $R_1$ in General Formulas (1) to (8).

Also, in General Formula (9), it is desirable that the substitution group bonds in the p-position relative to the hydroxyl group for the purpose of synthesis, if $b \leq 3$ or specifically R is subject to 3 substitutions or less, and a=1 or specifically the hydroxyl group is subject to one substitution, and also if at least one m-position of the hydroxyl group is not substituted. It is also desirable that the substitution group bonds in the o-position relative to the hydroxyl group for the purpose of synthesis if b=4 or specifically R is subject to 4 substitutions.

Accordingly, specific examples of a substituted phenyl group expressed by the aforementioned General Formula (9) or (10) where a=1 or there is one hydroxyl group include, among others, 4-hydroxyphenyl group, 3-methyl-4-hydroxyphenyl group, 2-methyl-4-hydroxyphenyl group, 2,5-dimethyl-4-hydroxyphenyl group, 3,5-dimethyl-4-hydroxyphenyl group, 2,3,5-trimethyl-4-hydroxyphenyl group, 3-ethyl-4-hydroxyphenyl group, 3-isopropyl-4-hydroxyphenyl group, 3-t-butyl-4-hydroxyphenyl group, 5-t-butyl-2-methyl-4-hydroxyphenyl group, 3,5-di-t-butyl-4-hydroxyphenyl group, 3-sec-butyl-4-hydroxyphenyl group, 3-tert-octyl-4-hydroxyphenyl group, 3-t-butyl-5-methyl-4-hydroxyphenyl group, 3-cyclohexyl-4-hydroxyphenyl group, 2-methyl-5-cyclohexyl-4-hydroxyphenyl group, 5-methyl-2-hydroxyphenyl group, 4,6-dimethyl-2-hydroxyphenyl group, 3,4,6-trimethyl-2-hydrorxyphenyl group, 3,5-di-t-butyl-2-hydroxyphenyl group, 5-tert-octyl-2-hydroxyphenyl group, 3-methoxy-4-hydroxyphenyl group, 3-n-hexyloxy-4-hydroxyphenyl group, 3-n-octyloxy-4-hydroxyphenyl group, and 5-butoxy-2-hydroxyphenyl group, while examples where a=2 or more or specifically there are two or three hydroxyl groups include, among others, 2,4-dihydroxyphenyl group, 3,4-dihydroxyphenyl group, 2-methyl-4,5-dihydroxyphenyl group, 3-methyl-4,5-dihydroxyphenyl group, 3-methyl-2,4-dihydroxyphenyl group, 5-methyl-2,4-dihydroxyphenyl group and 2,3,4-trihydroxyphenyl group.

Therefore, specific examples of a polynuclear polyphenol expressed by General Formula (11) or (12) include, among others:

1-[α-methyl-α-(3-bis(2,5-dimethyl-4-hydroxyphenyl)methyl-5-methyl-4-hydroxyphenyl)ethyl]-4-[α,α-bis(3-bis(2,5-dimethyl-4-hydroxyphenyl)methyl-5-methyl-4-hydroxyphenyl)ethyl]benzene (Compound 11);

[Chemical 40]

(Chemical Formula 11)

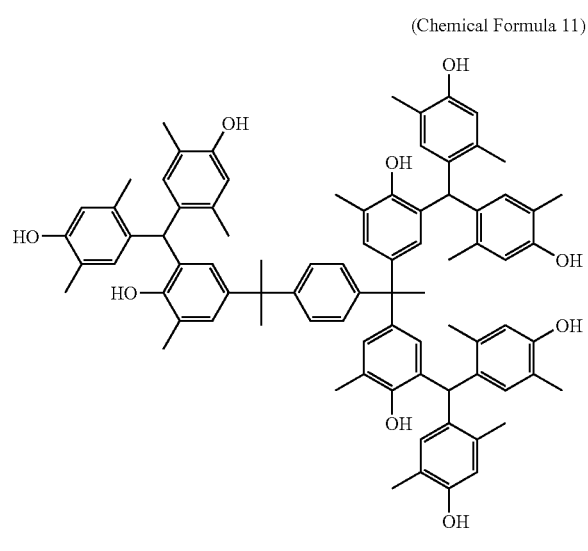

1-[α-methyl-α-(3-bis(3-methyl-4-hydroxyphenyl)methyl-5-methyl-4-hydroxyphenyl)ethyl]-4-[α,α-bis(3-bis(3-methyl-4-hydroxyphenyl)methyl-5-methyl-4-hydroxyphenyl)ethyl]benzene (Compound 12);

[Chemical 41]

(Chemical Formula 12)

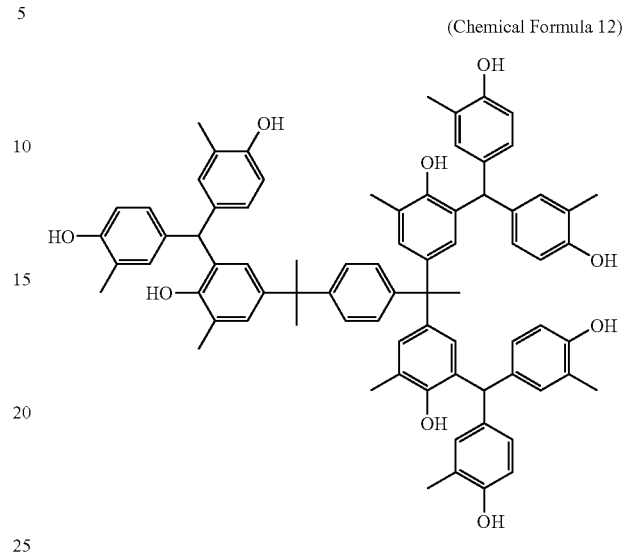

1-[α-methyl-α-(3-bis(2,3,5-trimethyl-4-hydroxyphenyl)methyl-5-methyl-4-hydroxyphenyl)ethyl]-4-[α,α-bis(3-bis(2,3,5-trimethyl-4-hydroxyphenyl)methyl-5-methyl-4-hydroxyphenyl)ethyl]benzene (Compound 13);

[Chemical 42]

(Chemical Formula 13)

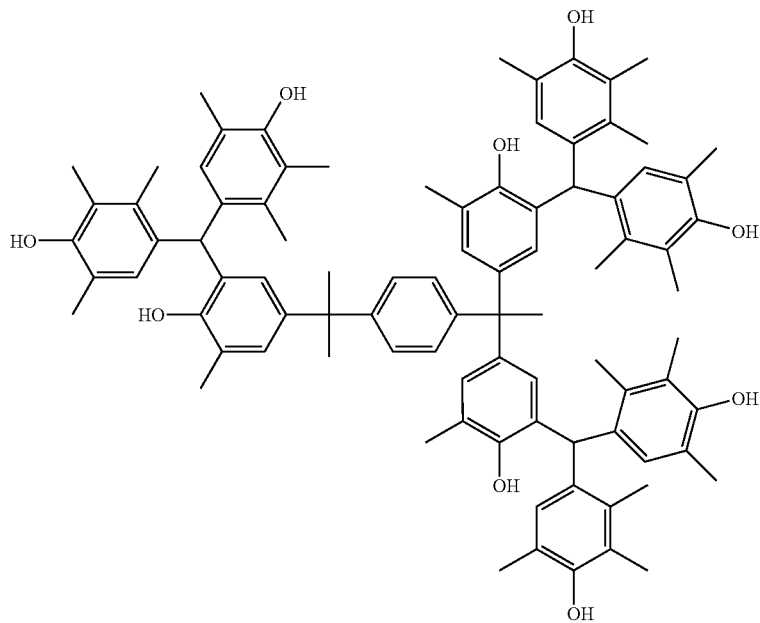

1-[α-methyl-α-(3-bis(2-methyl-5-cyclohexyl-4-hydroxyphenyl)methyl-5-methyl-4-hydroxyphenyl)ethyl]-4-[α,α-bis(3-bis(2-methyl-5-cyclohexyl-4-hydroxyphenyl)methyl-5-methyl-4-hydroxyphenyl)ethyl]benzene (Compound 14);

[Chemical 43]

(Chemical Formula 14)

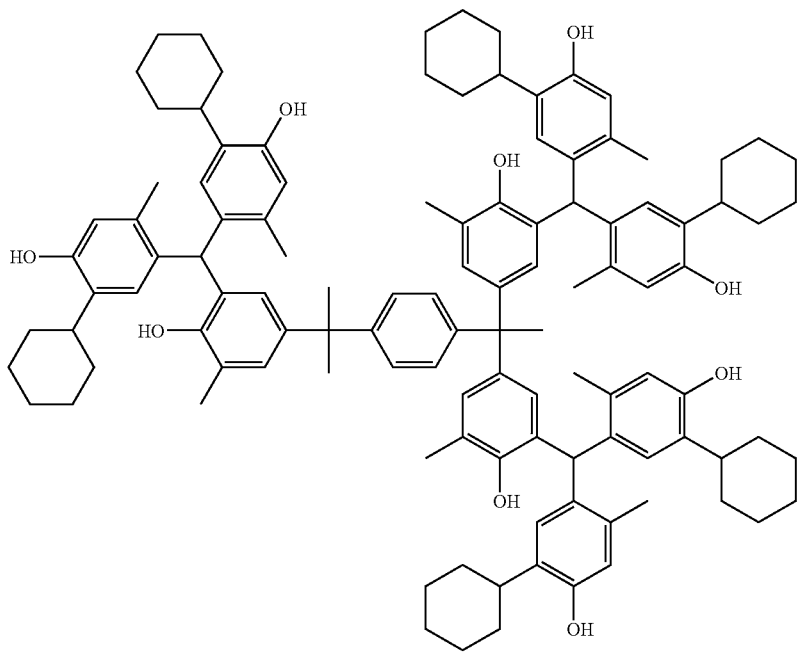

1-[α-methyl-α-(3-bis(3-tert-butyl-4-hydroxyphenyl)me-thyl-5-methyl-4-hydroxyphenyl)ethyl]-4-[α,α-bis(3-bis(3-tert-butyl-4-hydroxyphenyl)methyl-5-methyl-4-hydroxyphenyl)ethyl]benzene (Compound 15);

[Chemical 44]

(Chemical Formula 15)

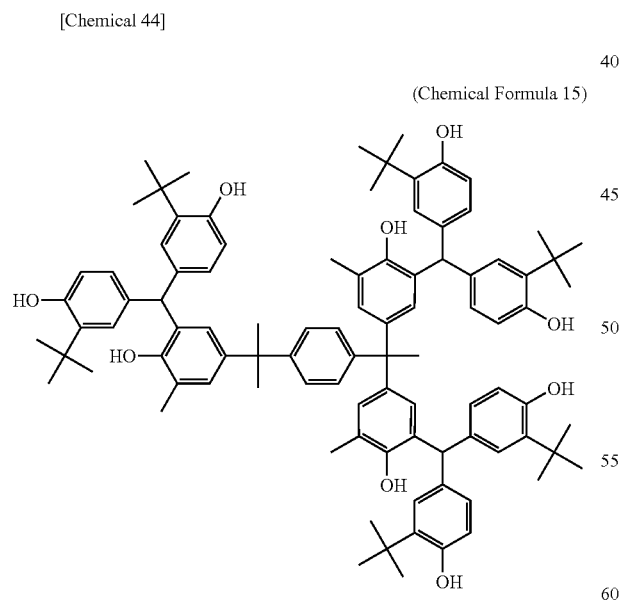

1-[α-methyl-α-(3-bis(2,5-dimethyl-4-hydroxyphenyl)me-thyl-5-isopropyl-4-hydroxyphenyl)ethyl]-4-[α,α-bis(3-bis(2,5-dimethyl-4-hydroxyphenyl)methyl-5-isopropyl-4-hydroxyphenyl)ethyl]benzene (Compound 16); and

[Chemical 45]

(Chemical Formula 16)

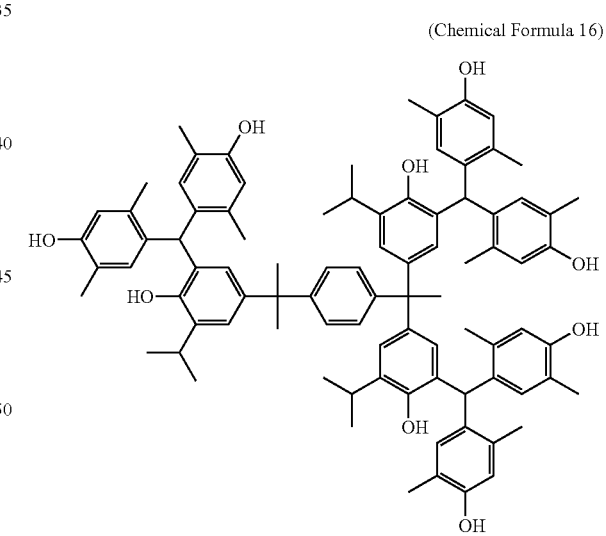

Other examples where
1-[α-methyl-α-(3-bis(2,5-dimethyl-4-hydroxyphenyl)me-thyl-5-methoxy-4-hydroxyphenyl)ethyl]-4-[α,α-bis(3-bis(2,5-dimethyl-4-hydroxyphenyl)methyl-5-methoxy-4-hydroxyphenyl)ethyl]benzene, 1-[α-methyl-α-(3-bis(2,5-dimethyl-4-hydroxyphenyl)me-thyl-5-cyclohexyl-4-hydroxyphenyl)ethyl]-4-[α,α-bis(3-bis(2,5-dimethyl-4-hydroxyphenyl)methyl-5-cyclohexyl-4-hydroxyphenyl)ethyl]benzene, 1-[α-methyl-α-(3-bis(3-tert-octyl-4-hydroxyphenyl)methyl-5-methyl-4-hydroxyphenyl)ethyl]-3-[α,α-bis(3-bis(3-tert-octyl-4-hydroxyphenyl)methyl-5-methyl-4-hydroxyphenyl)ethyl]benzene, 1-[α-methyl-α-(3-bis(3-n-octyloxy-4-hydroxyphenyl)methyl-5-methyl-4-hydroxyphenyl)ethyl]-4-[α,α-bis(3-bis(3-n-octyloxy-4-hydroxyphenyl)methyl-5-methyl-4-hydroxyphenyl)ethyl]benzene, 1-[α-methyl-α-(3-bis(5-methyl-2-hydroxyphenyl)methyl-5-methyl-4-hydroxyphenyl)ethyl]-4-[α,α-bis(3-bis(5-methyl-2-hydroxyphenyl)methyl-5-methyl-4-hydroxyphenyl)ethyl]benzene, 1-[α-methyl-α-(3-bis(3,4,6-trimethyl-2-hydroxyphenyl)methyl-5-methyl-4-hydroxyphenyl)ethyl]-4-[α,α-bis(3-bis(3,4,6-trimethyl-2-hydroxyphenyl)methyl-5-methyl-4-hydroxyphenyl)ethyl]benzene, 1-[α-methyl-α-(3-bis(4,6-dimethyl-2-hydroxyphenyl)methyl-5-methyl-4-hydroxyphenyl)ethyl]-4-[α,α-bis(3-bis(4,6-dimethyl-2-hydroxyphenyl)methyl-5-methyl-4-hydroxyphenyl)ethyl]benzene, 1-[α-methyl-α-(3-bis(3-methoxy-4-hydroxyphenyl)methyl-5-methyl-4-hydroxyphenyl)ethyl]-4-[α,α-bis(3-bis(3-methoxy-4-hydroxyphenyl)methyl-5-methyl-4-hydroxyphenyl)ethyl]benzene, 1-[α-methyl-α-(3-bis(2-methyl-4,5-dihydroxyphenyl)methyl-5-methyl-4-hydroxyphenyl)ethyl]-4-[α,α-bis(3-bis(2-methyl-4,5-dihydroxyphenyl)methyl-5-methyl-4-hydroxyphenyl)ethyl]benzene, and 1-[α-methyl-α-(3-bis(2,3,4-trihydroxyphenyl)methyl-5-methyl-4-hydroxyphenyl)ethyl]-4-[α,α-bis(3-bis(2,3,4-trihydroxyphenyl)methyl-5-methyl-4-hydroxyphenyl)ethyl]benzene.

Also when Y is a —$R_2COOR_3$ group in a trisformylphenyl group expressed by the aforementioned General Formula (8), the aforementioned General Formula (8) represents a polynuclear phenol expressed by General Formula (13) specified below,

[Chemical 46]

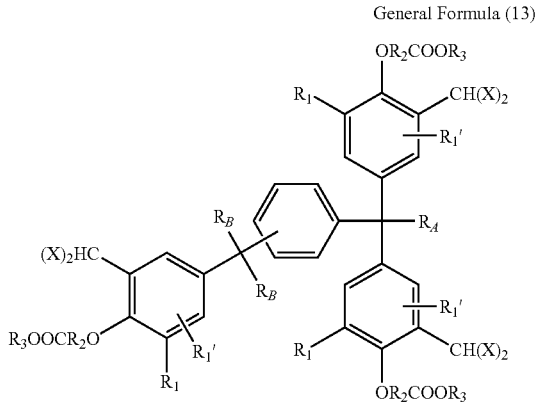

General Formula (13)

In the formula, $R_1$, $R_1'$, $R_2$, $R_3$, $R_A$, $R_B$ and X are the same as the items represented by the corresponding symbols in General Formula (8). Favorable examples of X are the same as those pertaining to the aforementioned General Formula (10).

A polynuclear phenol expressed by General Formula (14) specified below is a favorable example of a polynuclear phenol expressed by the aforementioned General Formula (13) where $R_1'$ is a hydrogen atom and $R_A$ and $R_B$ are methyl groups.

[Chemical 47]

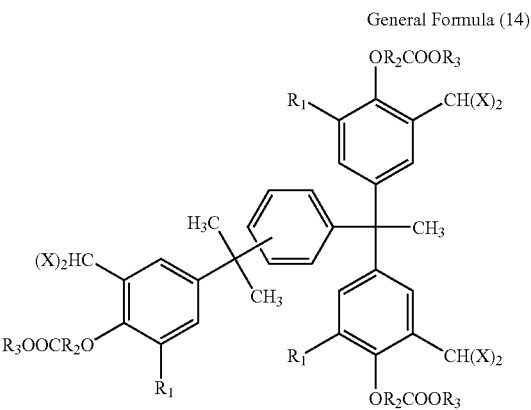

General Formula (14)

In the formula, $R_1$, $R_2$, $R_3$ and X are the same as the items represented by the corresponding symbols in General Formula (8). Favorable examples of X are the same as those pertaining to the aforementioned General Formula (10).

Accordingly, specific examples of a polynuclear phenol expressed by General Formula (13) or (14) include, among others:

1-[α-methyl-α-(3-bis(2,5-dimethyl-4-hydroxyphenyl)methyl-4-carboxymethoxy-5-methylphenyl)ethyl]-4-[α,α-bis(3-bis(2,5-dimethyl-4-hydroxyphenyl)methyl-4-carboxymethoxy-5-methylphenyl)ethyl]benzene (Compound 17);

[Chemical 48]

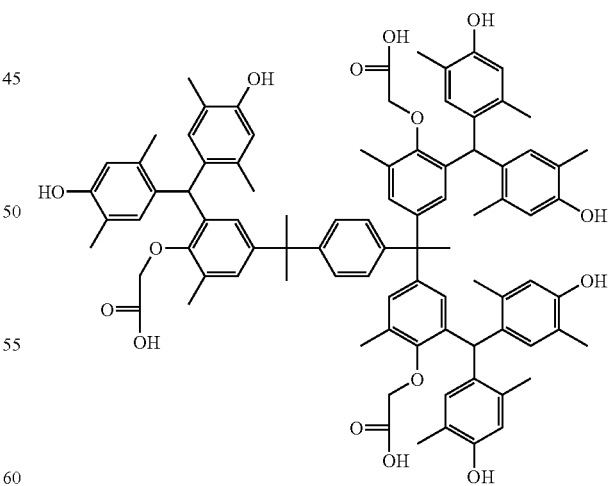

(Chemical Formula 17)

1-[α-methyl-α-(3-bis(2,5-dimethyl-4-hydroxyphenyl)methyl-4-(4-carboxyphenyl)methoxy-5-methylphenyl)ethyl]-4-[α,α-bis(3-bis(2,5-dimethyl-4-hydroxyphenyl)methyl-4-(4-carboxyphenyl)methoxy-5-methylphenyl)ethyl]benzene (Compound 18);

[Chemical 49]

(Chemical Formula 18)

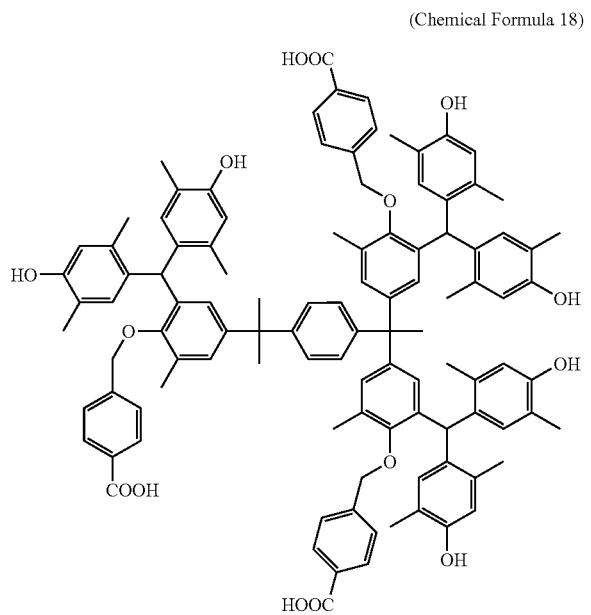

1-[α-methyl-α-(3-bis(2,5-dimethyl-4-hydroxyphenyl)methyl-4-(5-carboxy-1-naphtyl)methoxy-5-methylphenyl)ethyl]-4-[α,α-bis(3-bis(2,5-dimethyl-4-hydroxyphenyl)methyl-4-(5-carboxy-1-naphthyl)methoxy-5-methylphenyl)ethyl]benzene (Compound 19); and

[Chemical 50]

(Chemical Formula 19)

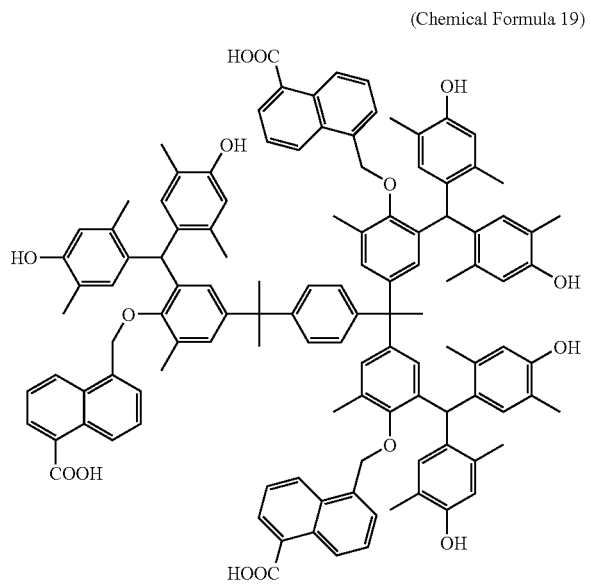

Other examples where
1-[α-methyl-α-(3-bis(2,3,5-trimethyl-4-hydroxyphenyl)methyl-4-methoxycarbonylmethoxy-5-methylphenyl)ethyl]-4-[α,α-bis(3-bis(2,3,5-trimethyl-4-hydroxyphenyl)methyl-4-methoxycarbonylmethoxy-5-methylphenyl)ethyl]benzene, 1-[α-methyl-α-(3-bis(2,3,5-trimethyl-4-hydroxyphenyl)methyl-4-(4-carboxyphenyl)methoxy-5-methylphenyl)ethyl]-4-[α,α-bis(3-bis(2,3,5-trimethyl-4-hydroxyphenyl)methyl-4-(4-carboxyphenyl)methoxy-5-methylphenyl)ethyl]benzene, 1-[α-methyl-α-(3-bis(2-methyl-5-cyclohexyl-4-hydroxyphenyl)methyl-4-carboxymethoxy-5-methylphenyl)ethyl]-3-[α,α-bis(3-bis(2-methyl-5-cyclohexyl-4-hydroxyphenyl)methyl-4-carboxymethoxy-5-methylphenyl)ethyl]benzene, 1-[α-methyl-α-(3-bis(2-methyl-5-cyclohexyl-4-hydroxyphenyl)methyl-4-(4-carboxyphenyl)methoxy-5-methylphenyl)ethyl]-4-[α,α-bis(3-bis(2-methyl-5-cyclohexyl-4-hydroxyphenyl)methyl-4-(4-carboxyphenyl)methoxy-5-methylphenyl)ethyl]benzene, 1-[α-methyl-α-(3-bis(2-methyl-5-cyclohexyl-4-hydroxyphenyl)methyl-4-carboxymethoxy-5-methylphenyl)ethyl]-4-[α,α-bis(3-bis(2-methyl-5-cyclohexyl-4-hydroxyphenyl)methyl-4-carboxymethoxy-5-methylphenyl)ethyl]benzene, 1-[α-methyl-α-(3-bis(3-methyl-4-hydroxyphenyl)methyl-4-(4-carboxyphenyl)methoxy-5-methylphenyl)ethyl]-4-[α,α-bis(3-bis(3-methyl-4-hydroxyphenyl)methyl-4-(4-carboxyphenyl)methoxy-5-methylphenyl)ethyl]benzene, 1-[α-methyl-α-(3-bis(3-t-butyl-4-hydroxyphenyl)methyl-4-(4-carboxyphenyl)methoxy-5-methylphenyl)ethyl]-4-[α,α-bis(3-bis(3-t-butyl-4-hydroxyphenyl)methyl-4-(4-carboxyphenyl)methoxy-5-methylphenyl)ethyl]benzene, 1-[α-methyl-α-(3-bis(2,5-dimethyl-4-hydroxyphenyl)methyl-4-carboxymethoxy-5-isopropylphenyl)ethyl]-4-[α,α-bis(3-bis(2,5-dimethyl-4-hydroxyphenyl)methyl-4-carboxymethoxy-5-isopropylphenyl)ethyl]benzene, 1-[α-methyl-α-(3-bis(2,5-dimethyl-4-hydroxyphenyl)methyl-4-carboxymethoxy-5-cyclohexyl phenyl)ethyl]-4-[α,α-bis(3-bis(2,5-dimethyl-4-hydroxyphenyl)methyl-4-carboxymethoxy-5-cyclohexylphenyl)ethyl]benzene, 1-[α-methyl-α-(3-bis(2,5-dimethyl-4-hydroxyphenyl)methyl-4-carboxymethoxy-5-methoxyphenyl)ethyl]-4-[α,α-bis(3-bis(2,5-dimethyl-4-hydroxyphenyl)methyl-4-carboxymethoxy-5-methoxyphenyl)ethyl]benzene, 1-[α-methyl-α-(3-bis(3-methoxy-4-hydroxyphenyl)methyl-4-carboxymethoxy-5-methylphenyl)ethyl]-4-[α,α-bis(3-bis(3-methoxy-4-hydroxyphenyl)methyl-4-carboxymethoxy-5-methylphenyl)ethyl]benzene, 1-[α-methyl-α-(3-bis(3,4,6-trimethyl-2-hydroxyphenyl)methyl-4-carboxymethoxy-5-methylphenyl)ethyl]-4-[α,α-bis(3-bis(3,4,6-trimethyl-2-hydroxyphenyl)methyl-4-carboxymethoxy-5-methylphenyl)ethyl]benzene, 1-[α-methyl-α-(3-bis(5-methyl-2-hydroxyphenyl)methyl-4-carboxymethoxy-5-methylphenyl)ethyl]-4-[α,α-bis(3-bis(5-methyl-2-hydroxyphenyl)methyl-4-carboxymethoxy-5-methylphenyl)ethyl]benzene, 1-[α-methyl-α-(3-bis(2-methyl-4,5-dihydroxyphenyl)methyl-4-carboxymethoxy-5-methylphenyl)ethyl]-4-[α,α-bis(3-bis(2-methyl-4,5-dihydroxyphenyl)methyl-4-carboxymethoxy-5-methylphenyl)ethyl]benzene, 1-[α-methyl-α-(3-bis(2,3,4-trihydroxyphenyl)methyl-4-carboxymethoxy-5-methylphenyl)ethyl]-4-[α,α-bis(3-bis(2,3,4-trihydroxyphenyl)methyl-4-carboxymethoxy-5-methylphenyl)ethyl]benzene, 1-[α-methyl-α-(3-bis(2,5-dimethyl-4-hydroxyphenyl)methyl-4-carboxymethoxy-2,5-dimethyl phenyl)ethyl]-4-[bis(3-bis(2,5-dimethyl-4-hydroxyphenyl)methyl-4-carboxymethoxy-2,5-dimethylphenyl)methyl]benzene, 1-[α-(3-bis(2,5-dimethyl-4-hydroxyphenyl)methyl-4-carboxymethoxy-5-methylphenyl)n-pentyl]-4-[α,α-bis(3-bis(2,5-dimethyl-4-hydroxyphenyl)methyl-4-carboxymethoxy-5-methylphenyl) n-butyl]benzene, 1-[α-(3-bis(3-methyl-4-hydroxyphenyl)methyl-4-carboxymethoxy-5-methylphenyl)ethyl]-4-[α,α-bis(3-bis(3-methyl-4-hydroxyphenyl)methyl-4-carboxymethoxy-5-methylphenyl)ethyl]benzene, and 1-[α-(3-bis(3-methyl-4-hydroxyphenyl)methyl-2-methoxy-4-carboxymethoxy-5-methylphenyl)ethyl]-3-[bis(3-bis(3-methyl-4-hydroxyphenyl)methyl-2-methoxy-4-carboxymethoxy-5-methylphenyl)methyl]benzene.

The production method for another novel compound, or polynuclear polyphenol, under the present invention derived from a tris(formylphenyl) expressed by the aforementioned General Formula (1) is not specifically limited. However, a favorable method is to use a tris(formylphenyl) expressed by General Formula (1) under the present invention as a direct material and cause it to react with a phenol in the presence of an acid catalyst, as illustrated by Reaction Formula (13) specified below where 1-[α-methyl-α-(3-formyl-5-methyl-4-hydroxyphenyl)ethyl]-4-[α,α-bis(3-formyl-5-methyl-4-hydroxyphenyl)ethyl]benzene (Compound 1) and 2,5-dimethylphenol are reacted with each other, or as illustrated by Reaction Formula (14) specified below where 1-[α-methyl-α-(3-formyl-5-methyl-4-methoxycarbonylmethoxyphenyl)ethyl]-4-[α,α-bis(3-formyl-5-methyl-4-methoxycarbonylmethoxyphenyl)ethyl]benzene and 2,5-dimethylphenol are reacted with each other.

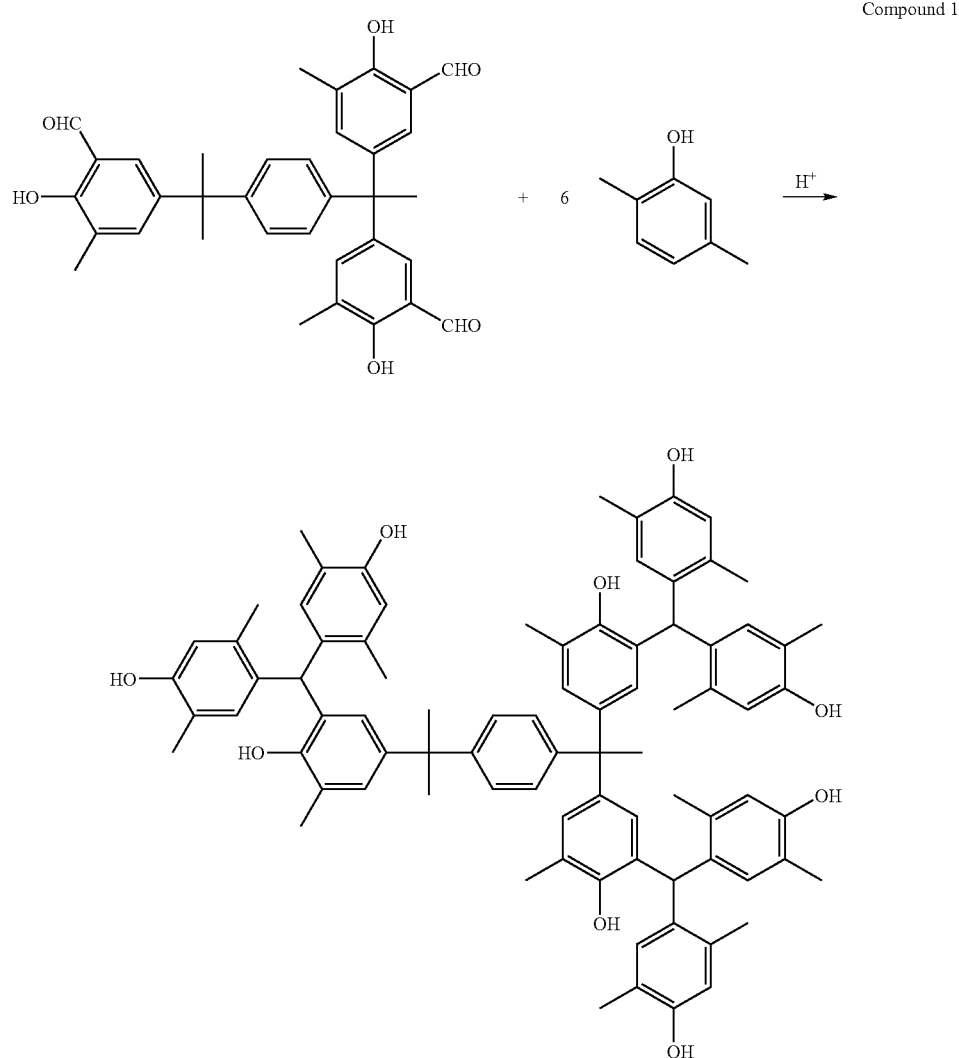

Reaction Formula (14)

[Chemical 52]

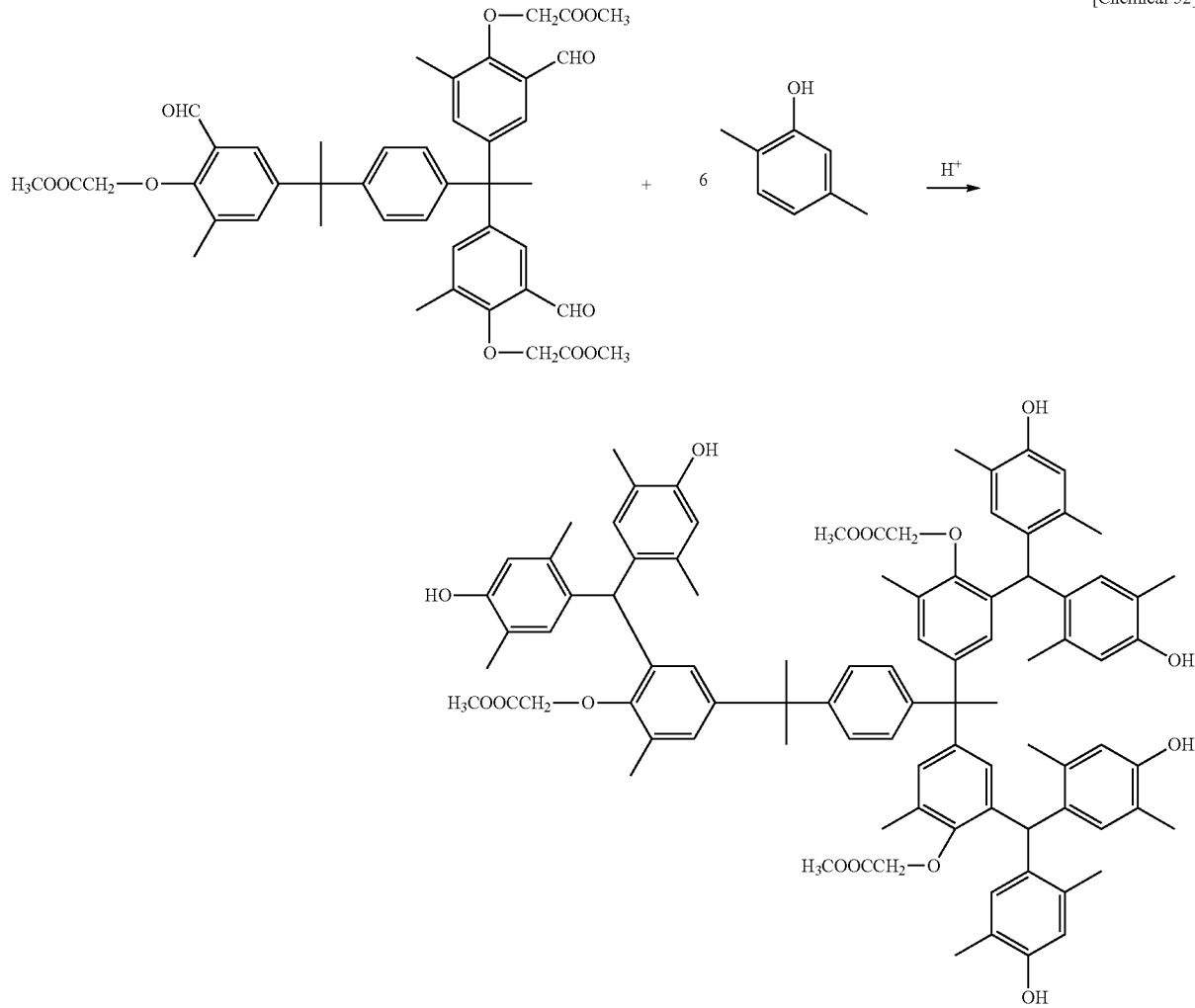

A phenol used above must have at least one of the o- and p-positions of the phenol nucleus remaining unsubstituted relative to the phenyl nucleus-substituted hydroxyl group. To be specific, a phenol whose p-position relative to the hydroxyl group is not substituted is desirable from the viewpoint of synthesis when there are three or less alkyl and/or alkoxyl group substitution groups and one hydroxyl group, or a phenol whose o-position relative to the hydroxyl group is not substituted is desirable from the viewpoint of synthesis when there are four alkyl and/or alkoxyl group substitution groups.

Accordingly, specific examples of phenols include, among others, those with one hydroxyl group such as phenol, o-cresol, p-cresol, m-cresol, 2,5-xylenol, 2,6-xylenol, 3,5-xylenol, 2,3,6-trimethylphenol, 2,3,5-trimethylphenol, 2-cyclohexyl-5-methylphenol, 2-cyclohexylphenol, 2-ethylphenol, 2-t-butylphenol, 2-t-butyl-5-methylphenol, 2,4-xylenol, 2,6-di-t-butylphenol, 2,4-di-t-butylphenol, 2-sec-butylphenol, 2-tert-octylphenol, 4-tert-octylphenol, 2-isopropylphenol, 2-t-butyl-4-methylphenol, 2-methoxyphenol, 4-butoxyphenol, 2-methyl-5-methoxyphenol, 2-n-hexyloxyphenol and 2-n-octyloxyphenol, as well as those having two or more hydroxyl groups such as resorcin, catechol, hydroquinone, 4-methylcatechol, 3-methylcatechol, 2-methylresorcinol, 4-methylresorcinol and pyrogallol.

In the aforementioned reaction of a tris(formylphenyl) with a phenol, an optimal amount of phenol to be added per 1 mol of tris(formylphenol) varies depending on the phenol used, but the range is normally 6 to 30 mols, or desirably 7 to 15 mols.

In the aforementioned reaction of a tris(formylphenyl) with a phenol, a reaction solvent may or may not be used. However, use of a solvent is desirable when the mol ratio of the tris(formylphenyl) to the phenol is small or the phenol has a high melting point and therefore the materials cannot be dissolved or agitated easily. Examples of reaction solvents that can be used include, among others, methanol, butanol and other lower aliphatic alcohols, toluene, xylene and other aromatic hydrocarbons, methyl isobutylketone and other aliphatic ketone, and mixtures thereof. Desirable solvents are lower aliphatic alcohols, and if catechol, resorcin or other phenol having a high melting point and high solubility in water is used, water may be used as a reaction solvent.

Although not specifically limited, such solvent should normally be used in a range of 0.1 to 10 parts by weight, or desirably in a range of 0.5 to 2 parts by weight, relative to the phenol used.

Under the production method illustrated by the aforementioned Reaction Formula (13) or (14), the aforementioned acid catalyst should desirably be an acid that dissolves in the reaction mixture. Accordingly, inorganic acids or organic acids such as organic sulfonic acids and carbonic acids of strong to medium acidity can be used. Specific examples include, among others, 35% hydrochloric acid, hydrogen chloride gas, sulfuric acid, phosphoric acid and other inorganic acids, or p-toluene sulfonic acid, methane sulfonic acid, oxalic acid and other organic acids. Although their desirable amount of use varies depending on the acidity, etc., normally these acid catalysts are used in a range of 1 to 50 percent by weight relative to the phenol.

The reaction is normally implemented for around 1 to 20 hours under agitation in air, or desirably in an atmosphere of nitrogen or other inert gas, in a temperature range of 0 to 100° C. or desirably 20 to 60° C.

Under the present invention, normally a polynuclear polyphenol compound produced by the reaction is refined and separated as necessary.

To this end, after the reaction an aqueous sodium hydroxide solution or other alkali water is added to the obtained reaction to neutralize the acid and then toluene, xylene, methyl isobutyl ketone, ether or other solvent that can be separated from water is added to separate and remove the water layer, after which the water layer is separated while the oil layer is washed and the solvent and unreacted material phenol are distilled out from the obtained oil layer as necessary, and then a solvent is added to achieve crystallization or precipitation/filtering to obtain crystal or non-crystal solids. If necessary, a similar crystallization or precipitation operation can be repeated once or multiple times to obtain a higher-purity product.

If the target reaction product, or polynuclear phenol compound, cannot be easily removed through the aforementioned crystallization or precipitation, then column separation or refining may be used, or in the aforementioned refining process the oil layer in which the compound is dissolved may be distilled, etc., to remove the solvent and thus obtain the target as a resin or resinous composition.

If the polynuclear phenol compound according to the aforementioned General Formula (8) is a polynuclear phenol compound expressed by the aforementioned General Formula (13), the production method to obtain a carboxyhydrocarbonoxy substituent where $R_3$ is a hydrogen atom is not specifically limited. However, a production method similar to the one illustrated by the aforementioned Reaction Formula (12) can be used to implement ester-hydrolysis using sodium hydroxide, tetramethylammonium hydroxide or other aqueous alkali solution to easily obtain a carboxyhydrocarbonoxy substituent (—O—$R_2$COOH) from an alkoxycarbonylhydrocarbonoxy substituent (—O—$R_2$COO$R_3$) being a polynuclear phenol compound whose $R_3$ in the 4-ether group is a primary or secondary alkyl group.

Also, the obtained reaction production can be refined, or a high-purity product may be obtained, if necessary, according to any known method. In this case, hydrolysis can be implemented easily when, as in the case of the aforementioned tris(4-ether-3-formylphenyl), the $R_3$ group in the (—$R_2$COO$R_3$) group of the alkoxycarbonyl hydrocarbon group is a primary alkyl group, and therefore it is preferable.

Effects of the Invention

A novel tris(formylphenyl) compound conforming to the present invention has three phenyl nuclei bonded asymmetrically to the central, asymmetrical dialkylbenzene skeleton that does not contain any acid-unstable unsaturated bond, where each phenyl nucleus has one formyl group and one hydroxyl group, and thus offers excellent heat resistance and reactivity, especially reactivity with phenols and other aromatic compounds, and can be used favorably as a photosensitive resin material, phenol resin, and other modifier, or reactive intermediate material for various polynuclear aromatic compounds, etc. Also, another embodiment of a novel tris(formylphenyl) compound conforming to the present invention has a structure where 4-ether-3-formylphenyl groups are bonded asymmetrically to the central dialkylbenzene skeleton, with each of the three terminal phenyl nuclei of the molecule having a formyl group and a hydroxyl group that has a substitution group etherified by a hydrocarbon group having an ester group or carboxyl group, and thus offers excellent reactivity due to the formyl group or excellent reactivity due to the terminal ester or carboxyl group, and can be used favorably as a phenol resin or other modifier, photoresist material, intermediate material for various polynuclear phenol compounds obtained via reaction with a phenol, or reactive intermediate material for polynuclear aromatic compounds offering excellent heat resistance, etc.

Also, a polynuclear phenol compound conforming to the present invention, obtained from the aforementioned material, is useful as a material for EUV and other photosensitive resist compositions, material for phenol resins, epoxy resin material or hardener, developer or anti-fade agent used in thermosensitive recording materials, or sterilizer, fungicide, antioxidant, etc. Since it has an asymmetrical alkylbenzene skeleton at the center, the compound does not easily crystallize or precipitate in a solvent, and also has a high glass transition temperature. Accordingly, if used as a photosensitive resist material or additive, the compound is expected to provide a favorable pattern and improved resolution, and if used in a resin, the compound is expected to improve heat resistance, flexibility, water resistance, etc. Also, a polynuclear polyphenol compound conforming to the present invention has six phenolic hydroxyl groups of high reactivity in the same molecule, and depending on the embodiment three of which have an ester or carboxy group. Because of their selective reactivity and interactivity, the compound is expected to provide improved resolution and other excellent effects when used as a photosensitive resist material or additive.

BEST MODE FOR CARRYING OUT THE INVENTION

EXAMPLES

The present invention is explained in further detail using examples.

Example 1

Synthesis of 1-[α-methyl-α-(3-formyl-5-methyl-4-hydroxyphenyl)ethyl]-4-[α,α-bis(3-formyl-5-methyl-4-hydroxyphenyl)ethyl]benzene 410.4 g (3.6 mols) of trifluoroacetic acid was put in a four-way flask with a capacity of 1 liter and the reaction container was replaced by nitrogen, after which 92.4 g (0.66 mol) of hexamethylenetetramine was added at a temperature of approx. 30° C. and then 111.4 g (0.2 mol; purity 92.4% based on high-speed liquid chromatography) of 1-[α-methyl-α-(3-hydroxymethyl-5-methyl-4-hydroxyphenyl)ethyl]-4-[α,α-bis(3-hydroxymethyl-5-methyl-4-hydroxyphenyl)ethyl]benzene was added under agitation at a temperature of 60° C. over 2 hours to achieve reaction. After the entire quantity had been added, the mixture was agitated further for 5 hours at 85° C. to achieve reaction.

After the reaction, 240 g of water was added to the obtained liquid, which was then hydrolyzed for 1 hour at a temperature of 60° C. Viscous solids precipitated during this reaction. After the reaction, 220 g of toluene was added to the obtained reaction mixture and the mixture was heated to 70° C. to dissolve the solids, and then the mixture was kept stationary and the water layer was removed. 32.8 g of 16% aqueous sodium hydroxide solution was added to neutralize the obtained oil layer, and then water was added further to agitate the mixture, followed by a stationary period, and then the water layer was removed. The obtained oil layer was condensed to 10 kPa at a temperature of 70° C., and then 30 g of ethyl ester acetate was added to the obtained residual liquid. Next, the mixture was cooled to 50° C. and 200 g of cyclohexane was added, after which the mixture was cooled and precipitated solids were filtered and dried to obtain 52.7 g of target light yellow powder (purity 93.2% based on high-speed liquid chromatography). The yield with respect to the material trishydroxymethyl compound was 47.8%.

Melting point (differential scanning calorimetry, peak top): 143.0° C.

Molecular weight (mass spectrometry, APCI⁻): 549 (M–H)⁻

1H-NMR identification result (400 MHz, solvent: DMSO-d6)

TABLE 1

[Chemical 53]

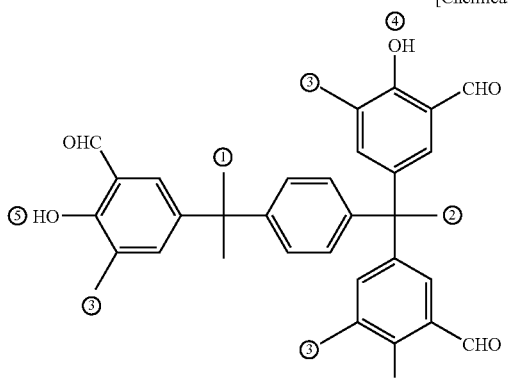

Proton NMR identification results (Internal standard: Tetramethylsilane)

| Shift value (ppm) | Proton number | Signal | Attribution |
|---|---|---|---|
| 1.64 | 6 | s | —CH₃(①) |
| 2.11 | 3 | s | —CH₃(②) |
| 2.14 | 9 | s | —CH₃(③) |
| 6.98~7.53 | 10 | m | Ph-H |

TABLE 1-continued

| | | | |
|---|---|---|---|
| 9.94 | 2 | s | PH-OH (④) |
| 10.02 | 1 | s | Ph-OH (⑤) |
| 10.92 | 3 | s | —CHO |

Example 2

Synthesis of 1-[α-methyl-α-(3-bis(2,5-dimethyl-4-hydroxyphenyl)methyl-5-methyl-4-hydroxyphenyl)ethyl]-4-[α,α-bis(3-bis(2,5-dimethyl-4-hydroxyphenyl)methyl-5-methyl-4-hydroxyphenyl)ethyl] benzene 44.0 g (0.36 mol) of 2,5-xylenol and 44 g of methanol were put in a four-way flask with a capacity of 1 liter and 35.2 g of hydrochloric acid gas was blown into the flask at a temperature of 30° C., after which a solution produced by dissolving 87.8 g (0.72 mol) of 2,5-xylenol in 175.6 g of methanol was drip-fed, and then 82.6 g (0.15 mol) of 1-[α-methyl-α-(3-formyl-5-methyl-4-hydroxyphenyl)ethyl]-4-[α,α-bis(3-formyl-5-methyl-4-hydroxyphenyl)ethyl]benzene obtained by Example 1 was added at a temperature of 30° C. over 1 hour 30 minutes to achieve reaction. After the reaction, the mixture was agitated further for 4 hours at a temperature of 40° C. to achieve reaction.

After the reaction, 241.2 g of 16% aqueous sodium hydroxide solution was added to neutralize the obtained reaction liquid, and then methanol was distilled out via concentration at normal pressure, after which 150 g of toluene, 100 g of ethyl acetate and 60 g of water were added and the mixture was heated to 70° C. under agitation, and then kept stationary to remove the water layer.

150 g of water was added to the obtained oil layer, followed by washing and separation using operations similar to those mentioned above, and the obtained oil layer was concentrated at normal pressure to distill out the solvent. Solids precipitated in the concentrate. Next, 200 g of water, 50 g of toluene and 60 g of ethyl acetate were added to the obtained residual liquid and the mixture was cooled and precipitated solids were filtered out to obtain 216.5 g of a crude product.

Next, the obtained crude product, 120 g of toluene, 300 g of ethyl acetate and 150 g of water were put in a four-way flask with a capacity of 1 liter and the mixture was heated to 70° C. to dissolve the crystal, after which the mixture was kept stationary to remove the water layer, and then 60 g of water was added to the obtained oil layer, followed by washing and separation using operations similar to those mentioned above. The obtained oil layer was concentrated at normal pressure to distill out 300 g of solvent, and then 100 g of water, 300 g of toluene and 70 g of ethyl acetate were added and the mixture was cooled to 25° C. to filter out and dry the precipitated solids to obtain 134.0 g of target light yellow-white powder (purity 98.6% based on high-speed liquid chromatography). The yield with respect to the material tris(formylphenol) was 72.6%.

Glass transition temperature (differential scanning calorimetry): 171.5° C.; no melting point observed Molecular weight (mass spectrometry, APCI⁻): 1229 (M–H)⁻

1H-NMR identification result (400 MHz, solvent: DMSO-d6)

TABLE 2

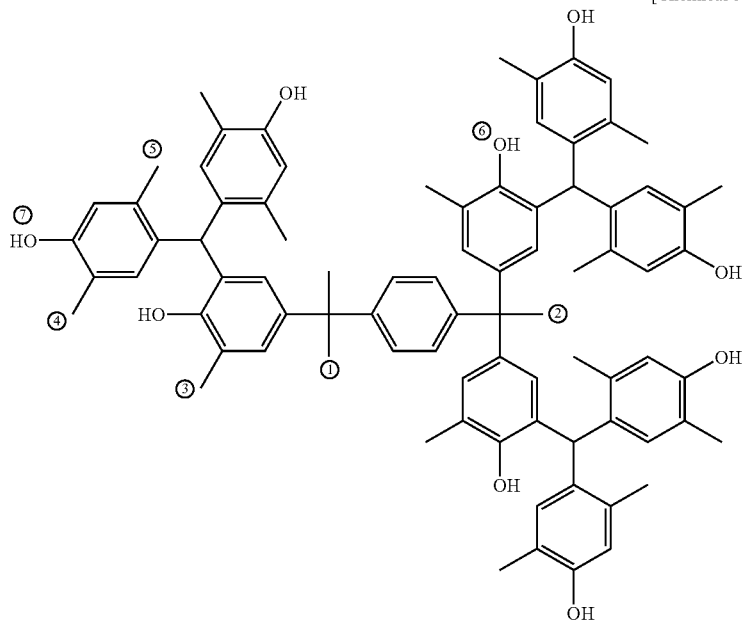

Proton NMR identification results (Internal standard: Tetramethylsilane)

| Shift value (ppm) | Proton number | Signal | Attribution |
|---|---|---|---|
| 1.37 | 6 | s | —CH$_3$(①) |
| 1.60 | 3 | s | —CH$_3$(②) |
| 1.78~1.98 | 45 | m | —CH$_3$(③) + (④) + (⑤) |
| 5.70~5.73 | 3 | m | —CH |
| 6.21~6.94 | 22 | m | Ph-H |
| 7.90~7.92 | 3 | m | Ph-OH (⑥) |
| 8.76~8.80 | 6 | m | Ph-OH (⑦) |

Example 3

Synthesis of 1-[α-methyl-α-(3-formyl-4-methoxy-carbonylmethoxy-5-methylphenyl)ethyl]-4-[α,α-bis(3-formyl-4-methoxycarbonylmethoxy-5-methylphenyl)ethyl]benzene 27.5 g (0.05 mol) of 1-[α-methyl-α-(3-formyl-5-methyl-4-hydroxyphenyl)ethyl]-4-[α,α-bis(3-formyl-5-methyl-4-hydroxyphenyl)ethyl]benzene obtained by Example 1 was put in a four-way flask with a capacity of 500 ml and the reaction container was replaced by nitrogen, after which 68.8 g of N-methylpyrrolidone was added to dissolve the material. Next, the solution was heated to 50° C., and then 2.75 g (0.017 mol) of iodinated potassium and 24.2 g (0.175 mol) of potassium carbonate were added and the mixture was agitated at the same temperature for 1 hour.

Next, the mixture was heated to 70° C., and 32.6 g (0.3 mol) of methyl acetate chloride was drip-fed over 1 hour. After the entire quantity had been added, the mixture was agitated further for 6 hours at 75° C. to achieve reaction.

After the reaction, 100 g of water and 120 g of toluene were added to the mixture liquid, followed by washing at 60° C., after which the water layer was removed and 50 g of water was added to the obtained oil layer, followed by three sets of washing and separation using similar operations. After the washing, the obtained oil layer was transferred into an eggplant flask and the solvent was distilled out at 70° C. under decompression to obtain 40.5 g of target brown liquid (purity 92.8% based on high-speed liquid chromatography). The yield with respect to the material tris(formylphenol) was 98.0%.

Molecular weight (mass spectrometry, APCI$^+$): 767 (M+H)$^+$

1H-NMR identification result (400 MHz, solvent: DMSO-d6, primary standard: Tetramethylsilane)

TABLE 3

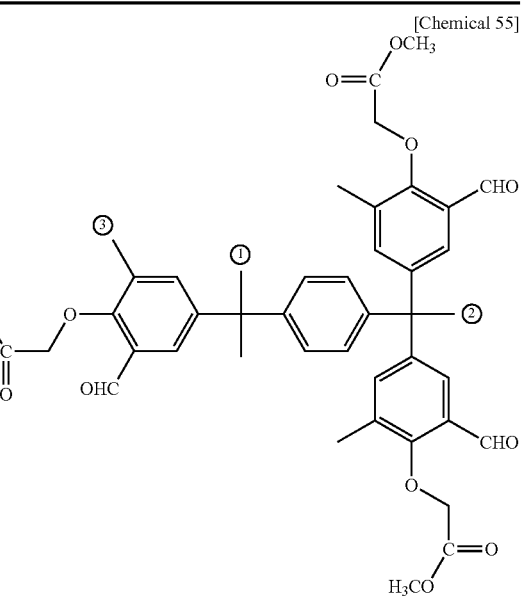

TABLE 3-continued

| Shift value (ppm) | Proton number | Signal | Attribution |
|---|---|---|---|
| 1.64 | 6 | s | —CH₃ (①) |
| 2.08-2.29 | 12 | m | —CH₃ ((②) + (③)) |
| 3.69-3.70 | 9 | m | —OCH₃ |
| 4.74-4.78 | 6 | m | —CH₂— |
| 6.95-7.48 | 10 | m | Ph-H |
| 10.34-10.36 | 3 | m | —CHO |

Example 4

Synthesis of 1-[α-methyl-α-(3-bis(2,5-dimethyl-4-hydroxyphenyl)methyl-4-carboxymethoxy-5-methylphenyl)ethyl]-4-[α,α-bis(3-bis(2,5-dimethyl-4-hydroxyphenyl)methyl-4-carboxymethoxy-5-methylphenyl)ethyl]benzene (Compound 11)

45.8 g (0.375 mol) of 2,5-xylenol, 55 g of methanol and 9.2 g of 35% aqueous hydrochloric acid solution were put in a four-way flask with a capacity of 1 liter and the reaction container was replaced by nitrogen, and then 40.5 g of liquid 1-[α-methyl-α-(3-formyl-4-methoxycarbonylmethoxy-5-methylphenyl)ethyl]-4-[α,α-bis(3-formyl-4-methoxycarbonylmethoxy-5-methylphenyl)ethyl]benzene obtained by Example 3 and 45 g of tetrahydrofuran were mixed, and the mixture was drip-fed over 1 hour 30 minutes. After the entire quantity had been dripped, the reaction mixture was heated to 40° C. and reacted for 22.5 hours under agitation.

After the reaction, 35.1 g of 25% aqueous tetramethylammonium hydroxide solution was added to neutralize the mixture solution which was then subjected to concentration at normal pressure to distill out and remove the solvent, after which 80 g of water and 120 of methyl isobutyl ketone were added to the concentrate, and then the solution was heated to 70° C. under agitation to separate the water layer and obtain the oil layer. 80 g of water was further added to the obtained oil layer, followed by washing and separation using similar operations. Thereafter, 98.4 g of 25% aqueous tetramethylammonium hydroxide solution was added to the obtained oil layer and the mixture was agitated for 30 minutes at 40° C. to achieve hydrolysis and separate the oil layer. 120 g of methyl isobutyl ketone and 180 g of 17.5% aqueous hydrochloric acid solution were added to the obtained water layer, after which the water layer was removed and 80 g of water was added further, followed by washing and separation using similar operations. The solvent was distilled out from the obtained oil layer at a temperature of 70° C. to obtain 37.3 g of target light yellow powder (purity 87.7% based on high-speed liquid chromatography). The yield with respect to the material tris(4-ether-3-formylphenyl) was 46.6%.

Glass transition temperature (differential scanning calorimetry): 158.5° C.; no melting point observed Molecular weight (mass spectrometry, APCI⁻): 1404 (M−H)⁻

1H-NMR identification result (400 MHz, solvent: DMSO-d6, primary standard: Tetramethylsilane)

TABLE 4

[Chemical 56]

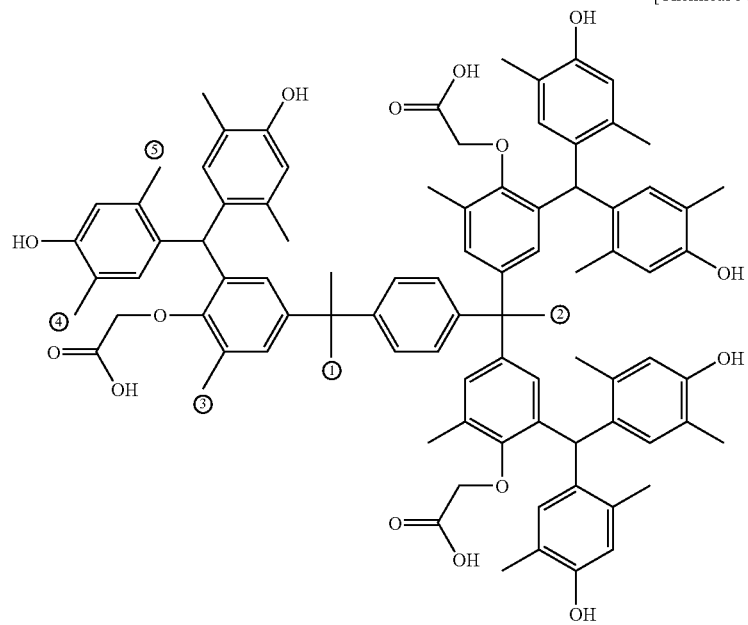

| Shift value (ppm) | Proton number | Signal | Attribution |
|---|---|---|---|
| 1.41 | 8 | m | CH₃ (①) |
| 1.73-2.30 | 48 | m | —CH₃ ((②) + (③) + (④) + (⑤)) |
| 3.80-3.89 | 8 | m | —CH₂ |
| 5.78-5.85 | 3 | m | —CH |
| 6.20-7.26 | 22 | m | Ph-H |
| 8.89-9.09 | 8 | m | Ph-OH |
| 12.76 | 3 | s | —COOH |

What is claimed is:

1. A tris(formylphenyl) expressed by General Formula (1):

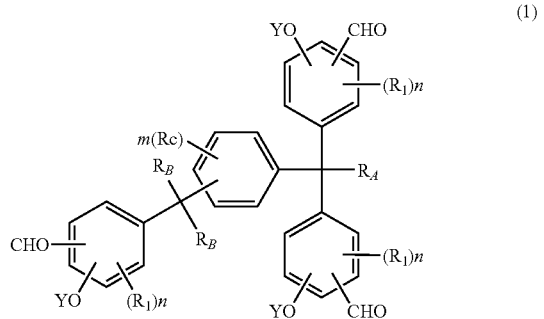

wherein Y represents a hydrogen atom or —R$_2$COOR$_3$ group, R$_2$ represents a monocyclic or condensed cyclic aromatic hydrocarbon group with a carbon atom number of 6 to 15 or an aliphatic hydrocarbon group with a carbon atom number of 1 to 8 that may have in its main chain a monocyclic or condensed cyclic aromatic hydrocarbon group with a carbon atom number of 6 to 15, and R$_3$ represents a hydrogen atom or alkyl group with a carbon atom number of 1 to 6; R$_1$s may be the same or different and respectively represent a hydrogen atom, alkyl group with a carbon atom number of 1 to 8 or alkoxyl group with a carbon atom number of 1 to 8; R$_B$ and R$_C$ may be the same or different, where R$_A$, R$_B$ and R$_C$ respectively represent a hydrogen atom or alkyl group with a carbon atom number of 1 to 6 and n and m are respectively an integer of 0 or 1 to 3.

2. The tris(formylphenyl) according to claim 1, expressed as a tris(formylphenol) according to General Formula (2):

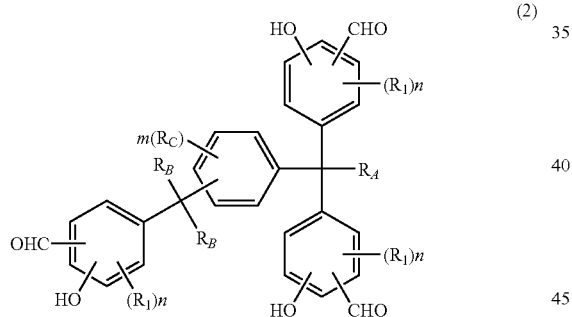

wherein R$_1$, R$_A$, R$_B$, R$_C$, n and m are the same as the items represented by the corresponding symbols in General Formula (1).

3. The tris(formylphenyl) according to claim 1, wherein General Formula (2) is represented by General Formula (3):

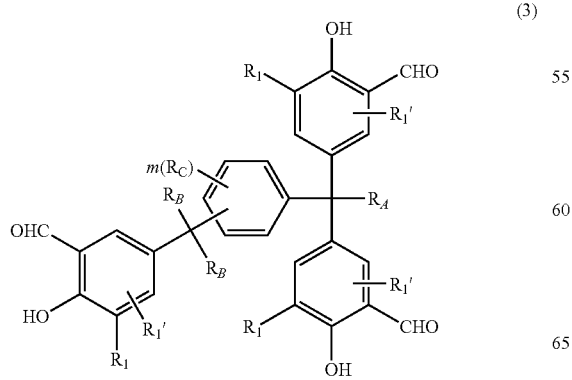

wherein R$_A$, R$_B$, R$_C$, R$_1$ and m are the same as the items represented by the corresponding symbols in General Formula (1); R$_1$' is the same as R$_1$ in General Formula (1) and represents a hydrogen atom, alkyl group with a carbon atom number of 1 to 8 or alkoxyl group with a carbon atom number of 1 to 8.

4. The tris(formylphenyl) according to claim 3, wherein General Formula (3) is represented by General Formula (4):

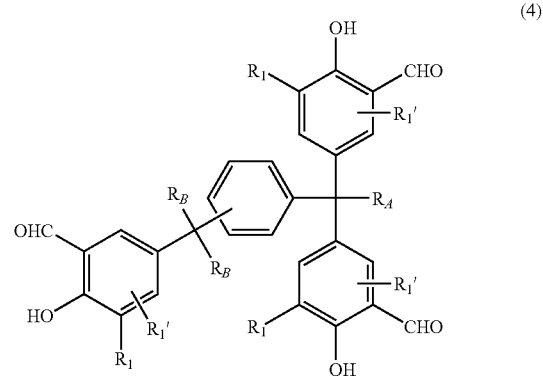

wherein R$_A$, R$_B$ and R$_1$ are the same as the items represented by the corresponding symbols in General Formula (1), and R$_1$' is the same as R$_1$ in General Formula (1).

5. The tris(formylphenyl) according to claim 4, wherein General Formula (4) is represented by General Formula (5):

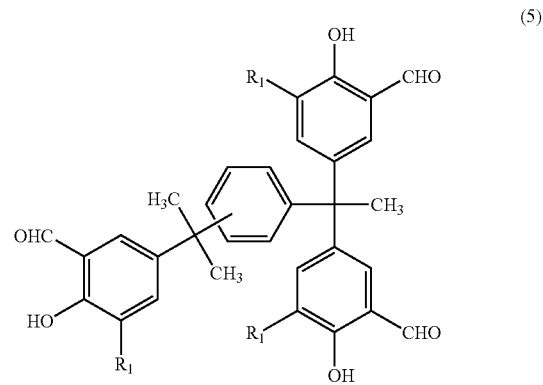

wherein R$_1$ is the same as the item represented by the corresponding symbol in General Formula (1).

6. The tris(formylphenyl) according to claim 1, expressed as a tris(4-ether-3-formylphenyl) according to General Formula (6):

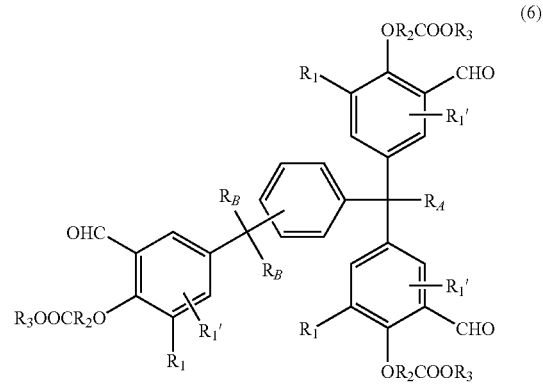

wherein $R_1$, $R_A$ and $R_B$ are the same as the items represented by the corresponding symbols in General Formula (1), and $R_1'$ is the same as $R_1$ in General Formula (1); $R_2$ and $R_3$ are the same as the items represented by the corresponding symbols in General Formula (1), where $R_2$ is a monocyclic or condensed cyclic aromatic hydrocarbon group with a carbon atom number of 6 to 15 or an aliphatic hydrocarbon group with a carbon atom number of 1 to 8 that may have in its main chain a monocyclic or condensed cyclic aromatic hydrocarbon group with a carbon atom number of 6 to 15; $R_3$ is a hydrogen atom or alkyl group with a carbon atom number of 1 to 6.

7. The tris(formylphenyl) according to claim 6, wherein General Formula (6) is represented by General Formula (7):

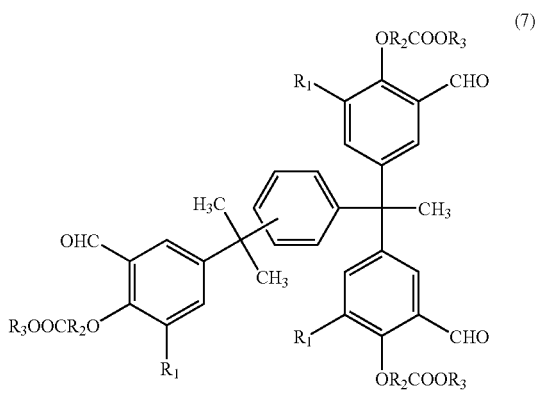

(7)

wherein $R_1$ $R_2$ and $R_3$ are the same as the items represented by the corresponding symbols in General Formula (6).

8. A polynuclear phenol expressed by General Formula (8):

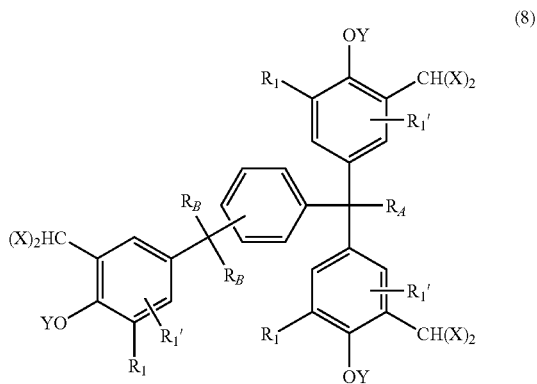

(8)

wherein $R_A$ and $R_B$ respectively represent a hydrogen atom or an alkyl group with a carbon atom number from 1 to 6; $R_1$ and $R_1'$ may be the same or different and respectively represent a hydrogen atom, an alkyl group with a carbon atom number from 1 to 8, or an alkoxyl group with a carbon atom number from 1 to 8; Y represents a hydrogen atom or —$R_2COOR_3$ group; $R_2$ represents a monocyclic or condensed cyclic aromatic hydrocarbon group with a carbon atom number of 6 to 15 or an aliphatic hydrocarbon group with a carbon atom number of 1 to 8 that may have in its main chain a monocyclic or condensed cyclic aromatic hydrocarbon group with a carbon atom number of 6 to 15; $R_3$ represents a hydrogen atom or primary or secondary alkyl group with a carbon atom number of 1 to 6; X represents a hydroxyphenyl group expressed by General Formula (9) specified below:

(9)

wherein R represents a hydrogen atom, alkyl group with a carbon atom number of 1 to 8 or alkoxyl group with a carbon atom number of 1 to 8, while a indicates an integer of 1 to 3 and b indicates an integer of 0 to 4, where $1 \leq a+b \leq 5$ and if b is 2 or more, Rs may be the same or different.

9. The polynuclear phenol according to claim 8, wherein General Formula (9) is represented by General Formula (10):

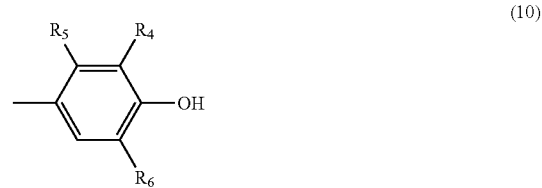

(10)

wherein $R_4$, $R_5$ and $R_6$ are the same as R in General Formula (9).

10. The polynuclear phenol according to claim 8, expressed by General Formula (11):

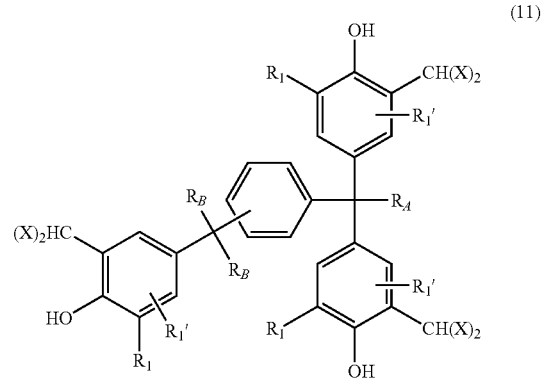

(11)

wherein $R_1$, $R_1'$, $R_A$, $R_B$ and X are the same as the items represented by the corresponding symbols in the aforementioned General Formula (8).

11. The polynuclear phenol according to claim 10, wherein General Formula (11) is represented by General Formula (12):

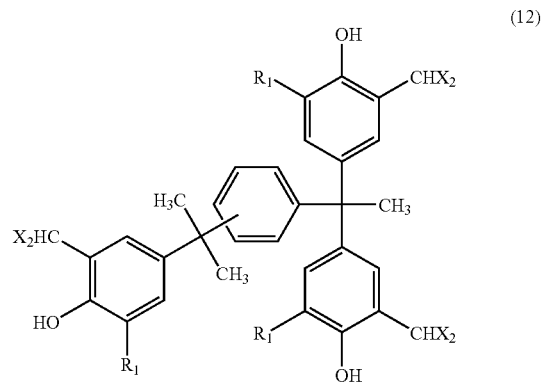

(12)

wherein $R_1$ and X are the same as the items represented by the corresponding symbols in the aforementioned General Formula (11).

12. The polynuclear phenol according to claim 8, expressed by General Formula (13):

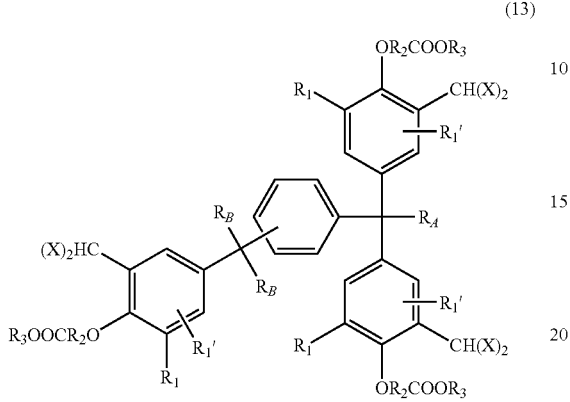

(13)

wherein $R_1$, $R_1'$, $R_2$, $R_3$, $R_A$, $R_B$ and X are the same as the items represented by the corresponding symbols in General Formula (8).

13. The polynuclear phenol according to claim 12, wherein General Formula (13) is represented by General Formula (14):

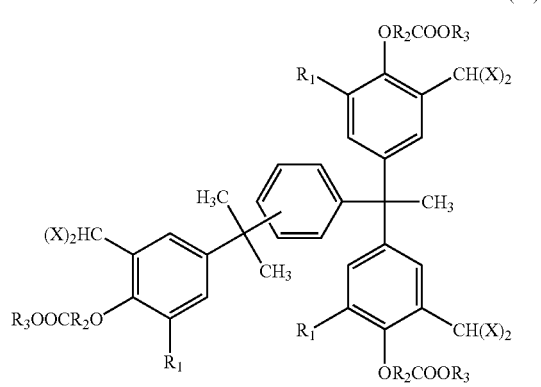

(14)

wherein $R_1$, $R_2$, $R_3$ and X are the same as the items represented by the corresponding symbols in General Formula (8).

* * * * *